US009763660B2

(12) United States Patent
Wazer et al.

(10) Patent No.: US 9,763,660 B2
(45) Date of Patent: *Sep. 19, 2017

(54) DELIVERY APPLICATOR FOR RADIOACTIVE STAPLES FOR BRACHYTHERAPY MEDICAL TREATMENT

(71) Applicant: Pointsource Technologies, LLC, Boston, MA (US)

(72) Inventors: David E. Wazer, Ashland, MA (US); Thomas A. DiPetrillo, Dover, MA (US)

(73) Assignee: Pointsource Technologies, LLC, Boston, MA (US)

( * ) Notice: Subject to any disclaimer, the term of this patent is extended or adjusted under 35 U.S.C. 154(b) by 167 days.

This patent is subject to a terminal disclaimer.

(21) Appl. No.: 14/581,071

(22) Filed: Dec. 23, 2014

(65) Prior Publication Data

US 2016/0361056 A1 Dec. 15, 2016
US 2017/0181744 A9 Jun. 29, 2017

Related U.S. Application Data

(60) Continuation of application No. 13/697,387, filed as application No. PCT/US2012/037015 on May 9, (Continued)

(51) Int. Cl.
*A61N 5/00* (2006.01)
*A61B 17/068* (2006.01)
(Continued)

(52) U.S. Cl.
CPC ........ *A61B 17/068* (2013.01); *A61B 17/0644* (2013.01); *A61B 17/0686* (2013.01);
(Continued)

(58) Field of Classification Search
CPC ...... A61N 5/00; A61N 5/1027; A61B 17/072; A61B 17/068
(Continued)

(56) References Cited

U.S. PATENT DOCUMENTS 7,604,586 B2 * 10/2009 Wazer .................. A61N 5/1027
600/3

* cited by examiner

*Primary Examiner* — John Lacyk
(74) *Attorney, Agent, or Firm* — David Driscoll, Esq.

(57) ABSTRACT

An instrument used for brachytherapy delivery in the treatment of cancer by radiation therapy including a handle having first and second handle actuators; an end effector; and an instrument shaft that connects the handle with the end effector. The end effector has first and second adjacent disposed staple cartridges that each retain a set of staples. The first mechanism is for holding standard staples in a first array, and dispensing the standard staples under control of the corresponding first handle actuator. The second mechanism is for holding radioactive source staples in a second array, and dispensing said radioactive source staples under control of the corresponding second handle actuator. The actuating device is removably attachable to an actuator arm on a proximal end. A staple applicator cartridge holder is attached to the actuator arm on a distal end. The staple applicator cartridge is mountable in the holder and having a plurality of slots for mounting of radioactive source staples therein. An anvil therein crimps the staples.

25 Claims, 35 Drawing Sheets

Related U.S. Application Data

2012, now abandoned, which is a continuation of application No. 13/108,759, filed on May 6, 2011, now Pat. No. 8,833,631, and a continuation of application No. 13/158,549, filed on Jun. 13, 2011, now Pat. No. 8,267,849, which is a continuation-in-part of application No. 12/462,042, filed on Jul. 28, 2009, now Pat. No. 7,972,260, which is a division of application No. 11/732,315, filed on Apr. 3, 2007, now Pat. No. 7,604,586.

(60) Provisional application No. 60/792,733, filed on Apr. 18, 2006.

(51) Int. Cl.
*A61N 5/10* (2006.01)
*A61B 17/064* (2006.01)
*A61B 17/072* (2006.01)

(52) U.S. Cl.
CPC .. *A61N 5/1027* (2013.01); *A61B 2017/07235* (2013.01); *A61B 2017/07271* (2013.01); *A61N 2005/1024* (2013.01); *A61N 2005/1025* (2013.01)

(58) Field of Classification Search
USPC .............................. 600/1–8; 227/175.1–176.1
See application file for complete search history.

US 9,763,660 B2

DELIVERY APPLICATOR FOR RADIOACTIVE STAPLES FOR BRACHYTHERAPY MEDICAL TREATMENT

TECHNICAL FIELD

The present invention relates to an improved method and system for applying a radioactive source to a tissue site. More particularly, the present invention pertains to an improved delivery system based upon the incorporation of a radioactive seed by fastening means, such as a surgical staple. More specifically, the present invention pertains to an improved brachytherapy delivery system for applying a radioactive source to a tissue site. Even more particularly the present invention relates to a new instrument construction wherein a single stapler instrument is used for precisely applying both standard surgical staples, as well as brachytherapy source staples relative to a surgical margin.

BACKGROUND AND OBJECTS OF THE INVENTION

The incidence of lung cancer has been rising over the last half century, although the rate has decreased somewhat over the last decade because of increased publicity about the health risks. The American Cancer Society estimates the number of new cases in 2009 to exceed 219,000. Lung cancer is the leading cause of cancer deaths in the United States among both men and women, expected to reach 159,000 in 2009, claiming more lives than colon, prostate and breast cancer combined.[i]

Non-small cell lung cancer (NSCLC) is the most commonly diagnosed form of the disease, affecting 4 out of 5 patients. In United States, ~23% of patients present with early-stage (T1, T2) disease.[ii] In most cases, early stage NSCLC can be treated successfully with surgery if the cancer has not spread beyond the chest. Surgical resection is the definitive treatment and lobectomy is the procedure of choice.[iii, iv, v] Lobectomy is the most common type of lung cancer surgery, involving removal of an entire lobe of one lung. For these early stage NSCLC patients, lobectomy yields a 5-year survival rate of 65-77%. Locoregional recurrence occurs in 28% of T1N0 tumors submitted to thoractomy, with the highest initial failure rates detected in the ipsilateral hemithorax.[vi, vii] Unfortunately, some patients with this disease are poor candidates for lobectomy due to poor pulmonary health or other medical issues.

Stage I NSCLC patients with compromised cardiopulmonary status may undergo limited surgical resections in an attempt at lung preservation while achieving adequate resection margins.[viii] However, lesser resections have been associated with an increased risk of local recurrence, even for small peripheral tumors.[ix] Nonetheless, limited resection is viewed as an acceptable alternative for patients with poor physiologic reserve or of advanced age.[x, xi]

Though sublobar resection alone is associated with an increased incidence of post-operative disease recurrence, it is still advocated for high-risk patients in the absence of a good alternative. External beam radiation therapy has been used successfully to reduce the risk of local recurrence in these compromised patients.[xii] However, external beam radiation therapy further reduces pulmonary function because it generally requires the beam to pass through normal lung tissue to reach the target lesion. Some studies suggest that adding brachytherapy to the regimen can make a dramatic difference in outcomes.

Intraoperative brachytherapy has been shown to be an effective therapeutic modality for patients unable to undergo a surgical lobectomy; it is an alternative to external beam irradiation for patients who cannot tolerate further loss of lung function.[xiii, xiv]

The use of brachytherapy has been shown in several studies to have a clinical benefit for compromised lung cancer patients for whom more traditional surgical procedures, such as a lobectomy, are not an option. This is now the subject of a NIH-sponsored Phase III Clinical trial.[xv]

These candidate patients would undergo limited (sublobar) surgical resection (wedge resection) in an attempt at lung preservation while achieving adequate resection margins, followed by brachytherapy. Currently, brachytherapy is performed using $^{125}$Iodine seeds delivered at the time of surgery. Seeds have been deployed by a variety of techniques such as manually suturing stranded seeds,[xvi] manually delivering loose seeds via a Mick® applicator,[xvii] thoracoscopic placement of vicryl mesh imbedded with $^{125}$Iodine radioactive seeds,[xviii] and seed placement in the wedge resection margin using the da Vinci robotic system.[xix]

The problem with all of these techniques is the difficulty in precisely delivering the brachytherapy seeds intraoperatively to achieve the proper dose distribution and minimizing the radiation dose to the clinicians performing the procedure.

When removing non-small cell lung cancers, the most prevalent form of lung cancer, conventional staples are typically used for the procedure. Moreover, the use of radioactive sources are placed near the cancer site to provide a mode of treatment. In this regard, U.S. Pat. Nos. 7,604,586 and 7,972,260 disclose one mode of treatment using staples containing a radioactive material and the attachment of these staples near the surgical resection. Reference may also be made to the aforementioned patents for background discussions pertaining to brachytherapy procedures.

Accordingly, there is a need for a staple delivery applicator having means for the accurate placement of radioactive staples at surgical sites.

Another object of the present invention to provide an apparatus or instrument for incorporating a radioactive source into or with a surgical procedure means such as a surgical staple so that the radioactive source can be positioned substantially concurrently with the application of the surgical tissue securing means.

Still another object of the present invention is to provide a brachytherapy source-delivery system and instrument that facilitates the precise placement of brachytherapy sources relative to a surgical margin, assures the seeds remain fixed in their precise position for the duration of the treatment, overcomes the technical difficulties of manipulating the seeds through a narrow surgical incision inherent in minimally invasive procedures, and at the same time reduces the radiation dose to the clinicians.

A further object of the present invention is to provide a means for irradiating cancer tissue with the use of staples in lung, colorectal and gynecological cancers, for example.

It is another object of the present invention to provide an effective therapeutic modality for patients unable to undergo a surgical lobectomy; it is an alternative to external beam irradiation for patients who cannot tolerate further loss of lung function.

It is a further object of the present invention to provide a means to precisely deliver the brachytherapy sources intraoperatively to achieve the proper dose distribution and minimizing the radiation dose to the clinicians performing the procedure.

It is still a further object of the present invention to provide a means for precise placement of brachytherapy sources relative to the surgical margin, assuring the sources remain fixed in their precise positions for the duration of the treatment, overcoming the technical difficulties of manipulating the sources through the narrow surgical incision, and reducing the radiation dose to the clinicians.

It is yet a further object of the present invention to provide a delivery device having better shielding than the existing stapler cartridges, thereby providing greater safety to the physician and other operating room personnel.

It is yet a further object of the present invention to provide a device that reduces the possibility of mis-locating sources by reducing and/or by limiting the number of potential source positions to only dosimetrically useful positions, rather than all staple positions, and further locating the sources nearer to the center of the treatment volume rather than at its edge.

SUMMARY OF THE INVENTION

The present invention facilitates the precise placement of, for example, $^{125}$Iodine seeds relative to the surgical margin, assures the seeds remain fixed in their precise position for the duration of the treatment, overcomes the technical difficulties of manipulating the seeds through the narrow surgical incision, and reduces the radiation dose to the clinicians. The concepts of the present invention incorporate the radioactive $^{125}$Iodine seeds into a fastening means, preferably surgical staples, used in the surgical procedure. In this way, the seeds are concurrently secured in position directly adjacent to the surgical resection and remain immobile. They are precisely located relative to the resection, placed by a very convenient method eliminating the difficulties of working through the narrow surgical incision. The seed position is rigidly fixed, assuring that the dose distribution does not uncontrollably change over the duration of the treatment. This method permits the dose distribution to be precisely planned prior to the surgery to achieve the desired result. Insertion of the seeds in conjunction with the application of the staples also significantly reduces the dose to the clinician.

In accordance with the present invention the source delivery system is used in conjunction with a standard surgical stapling instrument, such as one that is presently used for video-assisted thoracoscopic surgery (VATS). By integrating a permanent brachytherapy source in a standard surgical stapling instrument, there is provided a single instrument to cut and seal lung tissue and simultaneously place a permanent radioactive seed implant. With the instrument of the present invention: (1) The source/staple does not compromise the pre-established parameters of standard surgical staple delivery systems; (2) Uses preferably the same materials, measurements, and spacing of existing surgical staples; (3) Is deliverable using currently available surgical spacing instruments; (4) Is easily assembled with the standard stapler cartridge and is readily sterilized; and (5) Can be deliverable with minimal radiation exposure to the physician and other operating-room personnel.

A staple delivery applicator for delivering radioactive staples during brachytherapy medical treatment has an actuating device for attaching source staples located distally from the actuating device. The actuating device is removably attachable to an actuator arm on a proximal end. A staple applicator cartridge holder is attached to the actuator arm on a distal end. The staple applicator cartridge is mountable in the holder and having a plurality of slots for mounting of radioactive source staples therein. An anvil therein crimps the staples. The staple applicator cartridge holder is removably mountable in a connector and the connector is also removably mounted to a surgical staple holder. In one embodiment a trigger device has a control for closing the anvil of the cartridge holder and for firing of the source staples in the cartridge therein to cause the staples to crimp, and a control for opening the anvil and releasing the trigger device from the actuator arm.

DESCRIPTION OF THE DRAWINGS

Numerous other objects, features and advantages of the present invention are now realized by a reading of the following detailed description taken in conjunction with the accompanying drawings, in which.

Like reference numerals refer to like parts throughout the several views of the drawings.

DETAILED DESCRIPTION

An objective of the present invention is to develop an improved delivery system based upon the incorporation of a radioactive seed into fastening means, preferably into a surgical staple. More particularly the disclosed system is an improved brachytherapy delivery system for treatment of, inter alia, lung cancer based upon the incorporation of radioactive seeds into surgical staples used in lung resection. For patients with compromised cardiopulmonary status, the inclusion of brachytherapy with sublobular resection has shown a significant improvement in therapeutic outcome over sublobular resection alone. This present technique facilitates the delivery of this therapy. Furthermore, the techniques described herein may also be used in other medical procedures. Moreover, the techniques of the present invention may be used in applying a variety of radioactive sources.

The technique of the present invention facilitates the precise placement of, for example, $^{125}$Iodine seeds relative to the surgical margin, assures the seeds remain fixed in their precise position for the duration of the treatment, overcomes the technical difficulties of manipulating the seeds through the narrow surgical incision, and reduces the radiation dose to the clinicians. The examples describe the use of Iodine-125 as the radiation source but this is understood to be illustrative and that any radionuclide commonly used for brachytherapy, including Palladium-103, Cesium-131 and Ytterbium-169 could be incorporated into these staple/sources.

The present invention develops a brachytherapy system that can be used for intraoperative placement of radioactive seeds simultaneously with fastener means, preferably surgical staples, used in lung wedge resection procedures. Such a instrument precisely fixes the position of the seeds relative to the resection margin and provide a well defined, stable dose distribution to the target, while facilitating the means for delivering these seeds with reduced dose to the physicians. In one embodiment this is performed by having the radiation source integral with the fastener or staple so that when the resection occurs, concurrently therewith, the radiation source is properly positioned.

Figure 1:
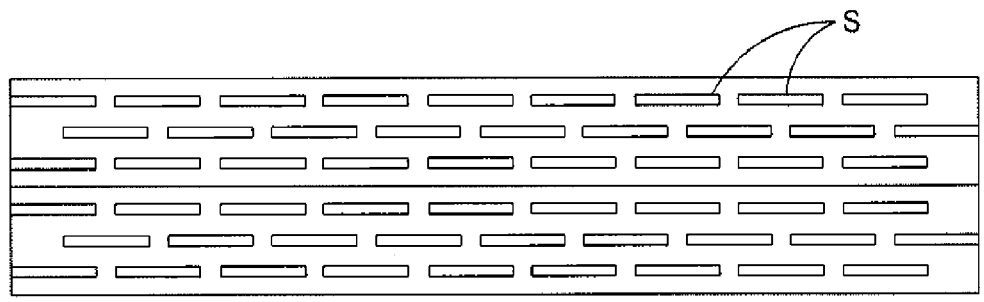
FIG. 1 is an example of the staple pattern in a typical surgical stapling system.

The instrument of the present invention permits delivery of the seeds and surgical staples using currently-available surgical stapling instruments modified in accordance with the principles of the present invention. The seed/staple combination is easily assembled with the staple cartridge. The combination is readily sterilizable. The combination is deliverable with minimal radiation exposure to the physician. The design of any additional structure around the $^{125}$Iodine seed should be sensitive to excessive modulation of the dosimetric parameters of the seed. Refer to FIG. 1 that illustrates an example of the staple pattern in a surgical stapling system.

Figure 2:
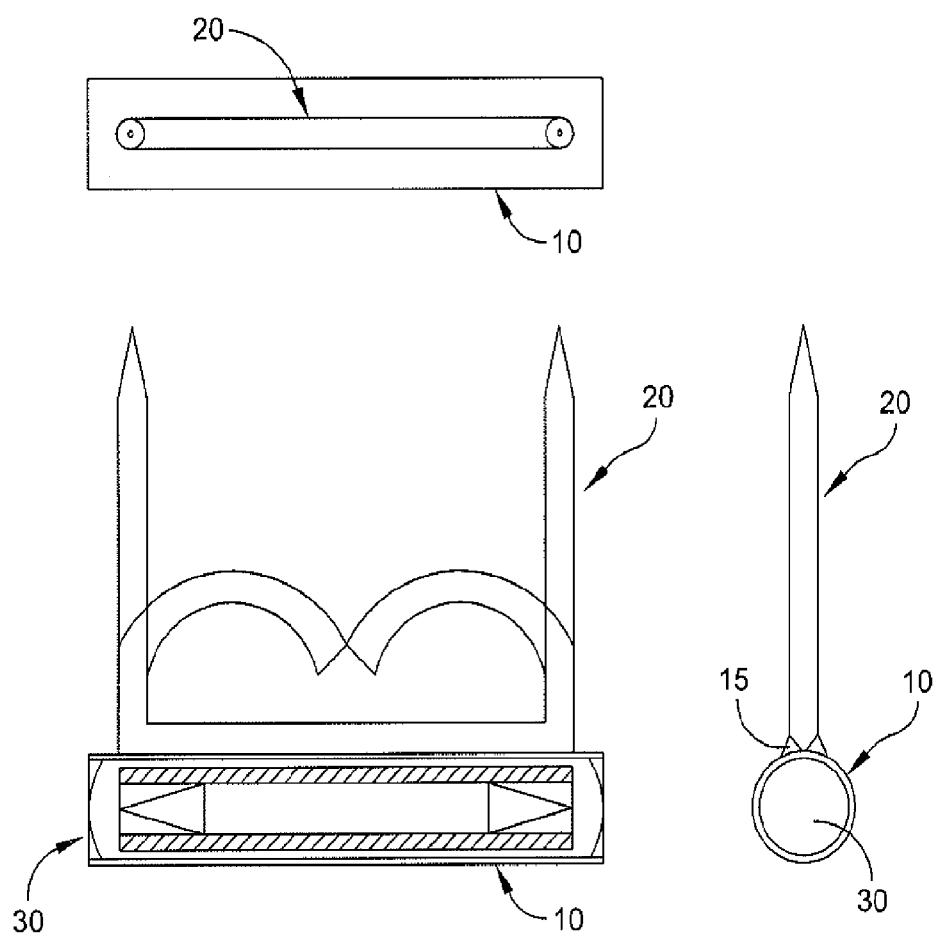
FIG. 2 is an illustration of a single staple that is attached with a retaining sleeve that accommodates a radioactive seed.

One embodiment of a source staple is shown in FIG. 2 and includes the attachment of a sleeve 11 to a single surgical staple 20 by means of laser welding at 15. The sleeve 10 may be of 0.9 mm OD.times.0.8 mm ID and accommodates a standard radioactive $^{125}$Iodine seed 30, as illustrated in FIG. 2. A standard seed is 4.5 mm long, which is longer than an individual staple. This could be accommodated in the cartridge in such a way as to not interfere with adjacent staples. The radioactive $^{125}$Iodine seed 30 is inserted and fixed within the sleeve 10. As noted in FIG. 2, the radioactive source and sleeve are preferably symmetrically located relative to the staple 20. FIG. 2 also shows the staple in both a rest position and a released bent position. It is noted that the legs of the staple are pointed as usual.

Figure 3:
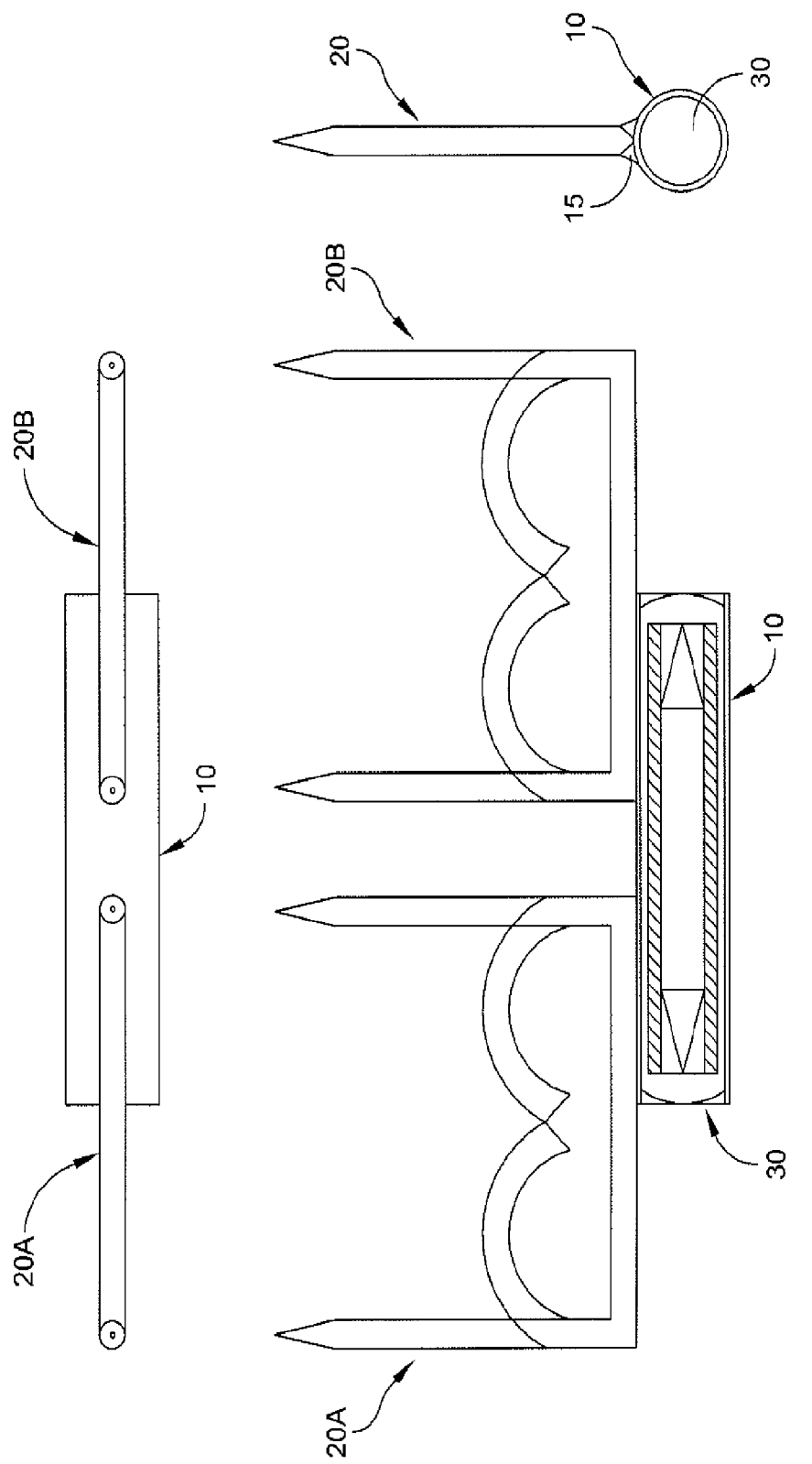
FIG. 3 is a further example, like that shown in FIG. 2, but using a pair of staples interconnected with a single sleeve.

An alternative embodiment, as shown in FIG. 3, illustrates the attachment of a sleeve 10 to two adjacent staples 20A and 20B, thereby accommodating the length and providing an additional measure of stability. As noted in FIG. 3, the sleeve is preferably symmetrically located relative to the pair of staples 20. The sleeve 10 bridges between the adjacently disposed staple pair, secured by means of the laser weld. The sleeve preferably is in contact with each staple over a like length so as to provide the symmetry. FIG. 3 also shows the staples in both a rest position and a released bent position. The system of the present invention provides an integral fastener in which the radiation source is integrally formed with the fastener, and usable in a surgical procedure.

Figure 4:
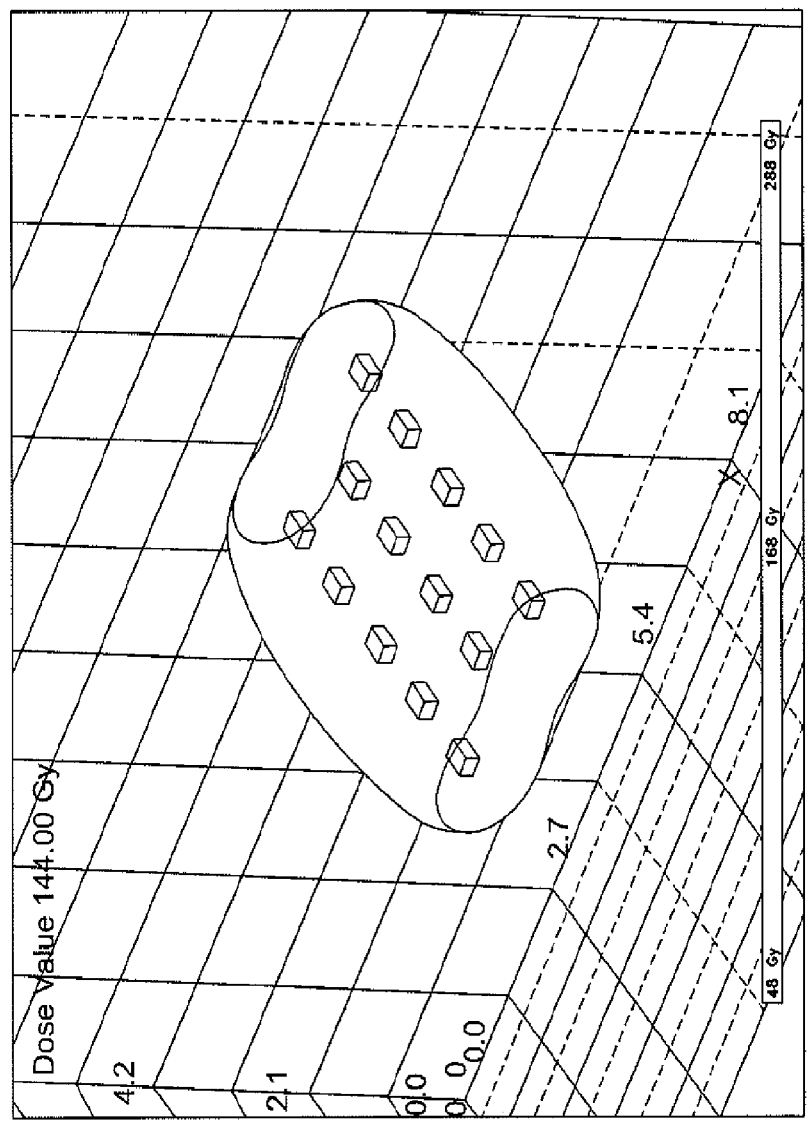
FIG. 4 illustrates a plan for a single resection, margin with an axially symmetric seed.

In most brachytherapy situations, this treatment plan could be performed using a standard treatment planning system. FIG. 4 shows a typical plan for a single resection margin using a standard treatment planning system with axially symmetric seed dosimetry. However, the I-Plant TPS, as well as all other commercial treatment planning software assume axially symmetric dose distributions in their calculational algorithms. Consequently, standard treatment planning software does not account for axial asymmetry and therefore does not provide precise results.

The cartridges for the surgical staples may be molded in plastic. This material does not provide any appreciable shielding, even for such a low energy radionuclide as $^{125}$Iodine. However, high density plastics containing tungsten are available and are regularly used for radiation shielding for $^{125}$Iodine seeds. We would plan to fabricate the special cartridge using this type of plastic. The cartridge would be designed to provide adequate shielding for the clinicians handling this instrument during the surgical procedure.

Figure 5:
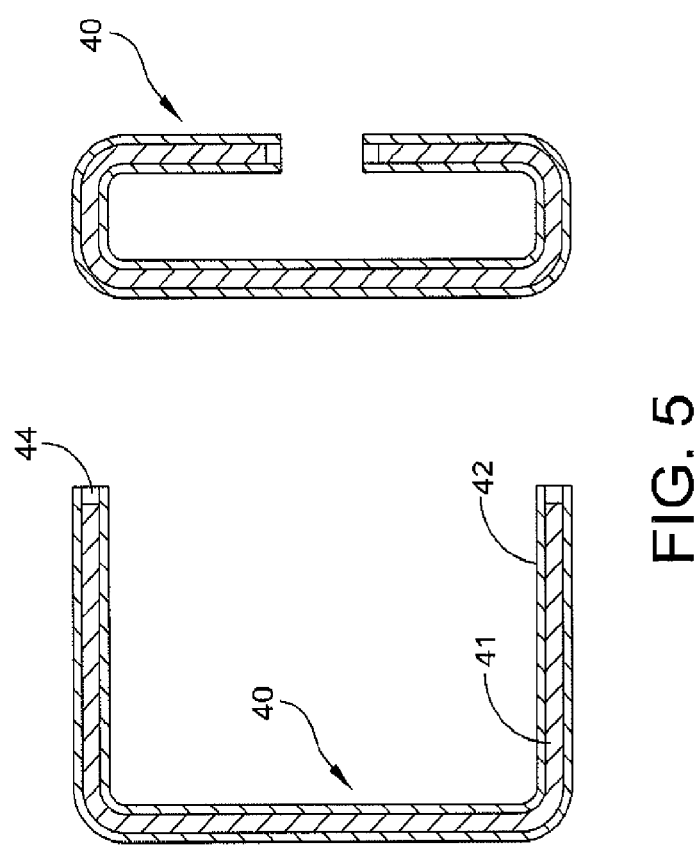
FIG. 5 illustrates another staple configuration.

Another embodiment in accordance with the present invention is shown in FIG. 5 and includes an integrally formed staple structure shown in both open and closed positions. This is comprised of a radioactive center element 41 and an encapsulating outer element 42. The ends 44 are shown blunt but in practice would be pointed so as to function as a surgical staple. The base of the staple is preferably about 3 inches and each leg, in the open position is about 2 inches. These can be readily accommodated in a conventional staple delivery cartridge.

Figure 6:
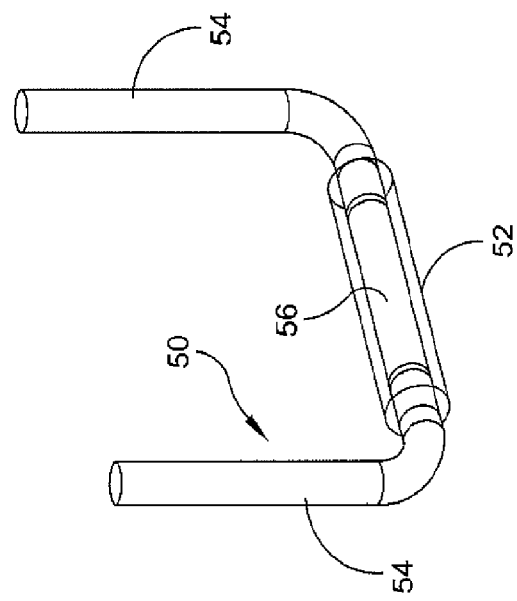
FIG. 6 illustrates still another staple configuration.
Figure 7:
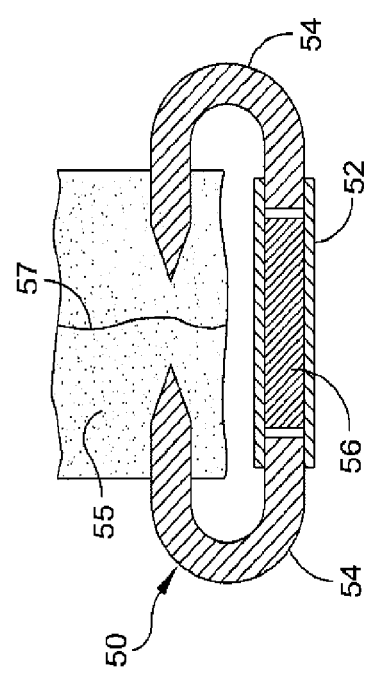
FIG. 7 is a cross-sectional view of the staple of FIG. 6 showing the staple closed to join tissue.
Figure 8:
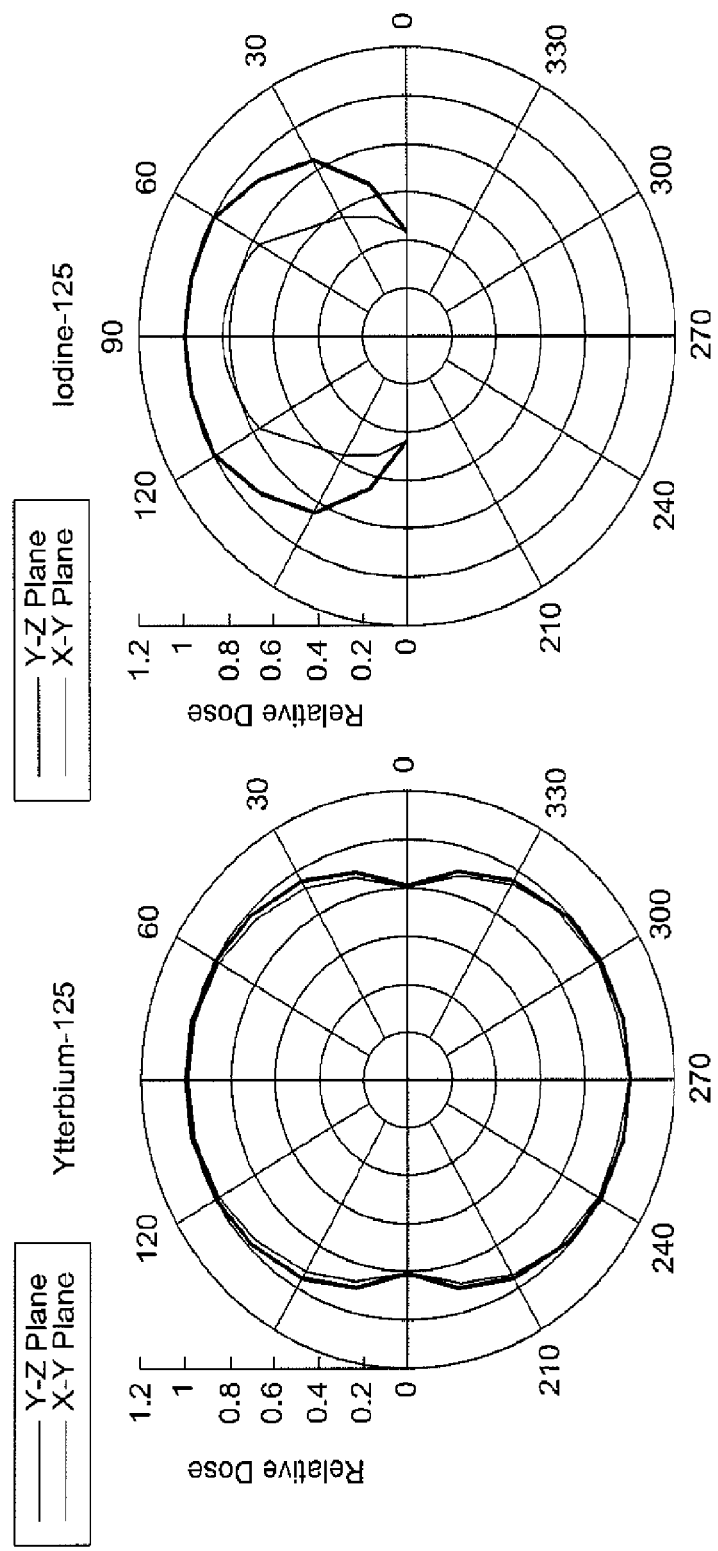
FIG. 8 illustrates dose distribution for the embodiment of FIG. 6.

Reference is now made to FIG. 6 for an illustration of still another embodiment that incorporates the radioactive material inside the staple itself by sealing it within a cavity created from a titanium tube. In FIG. 6 the staple is shown in both open and closed positions. Refer also to FIG. 7 for further details of this staple structure. FIG. 7 also illustrates the staple 50 as engaging a tissue 55 at incision 57. This staple 50 includes a cylindrical tube 52 that is preferably a titanium tube, but may also be of other metal materials. These materials include platinum, titanium, nickel-titanium alloys, gold, stainless steel, palladium, silica and alumina. The tube 52 defines a tubular cavity that is capped/sealed by titanium wires 54 that are laser-welded to the tube. The wires 54 serve as the legs of the staple.

In the embodiment shown in FIGS. 6 and 7 the radioactive material 56 is located inside the titanium tube which may be of ~0.40 mm in diameter with a wall thickness of ~0.07 mm, resulting in a cavity of 0.26 mm diameter. The ends of the tube 52 are plugged with titanium wires 54 of 0.25 mm diameter which may be laser-welded to the tubing. These wires 54 are typical of the wire-size currently used in surgical staples. Such a tubular capsule of 0.40 mm diameter readily fits within the cavity of currently-used staple delivery systems.

Figure 9:
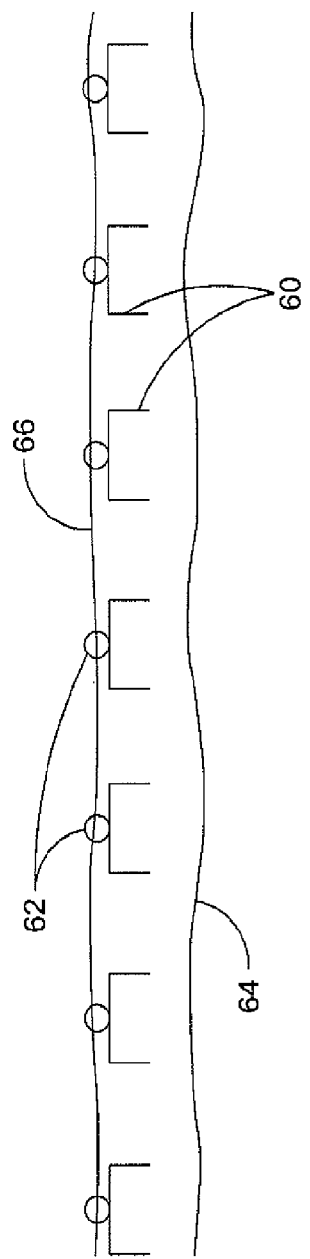
FIG. 9 schematically illustrates another embodiment of the present invention.
Figure 10:
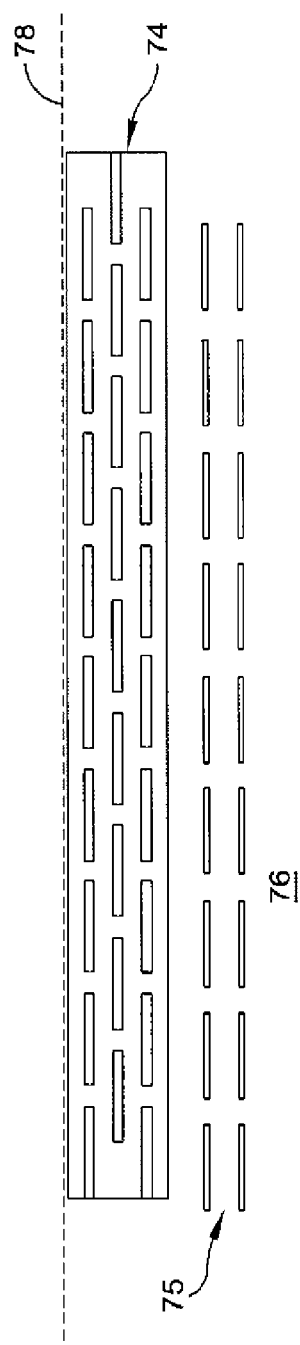
FIG. 10 schematically illustrates one standard staple array in parallel with a source array.
Figure 17:
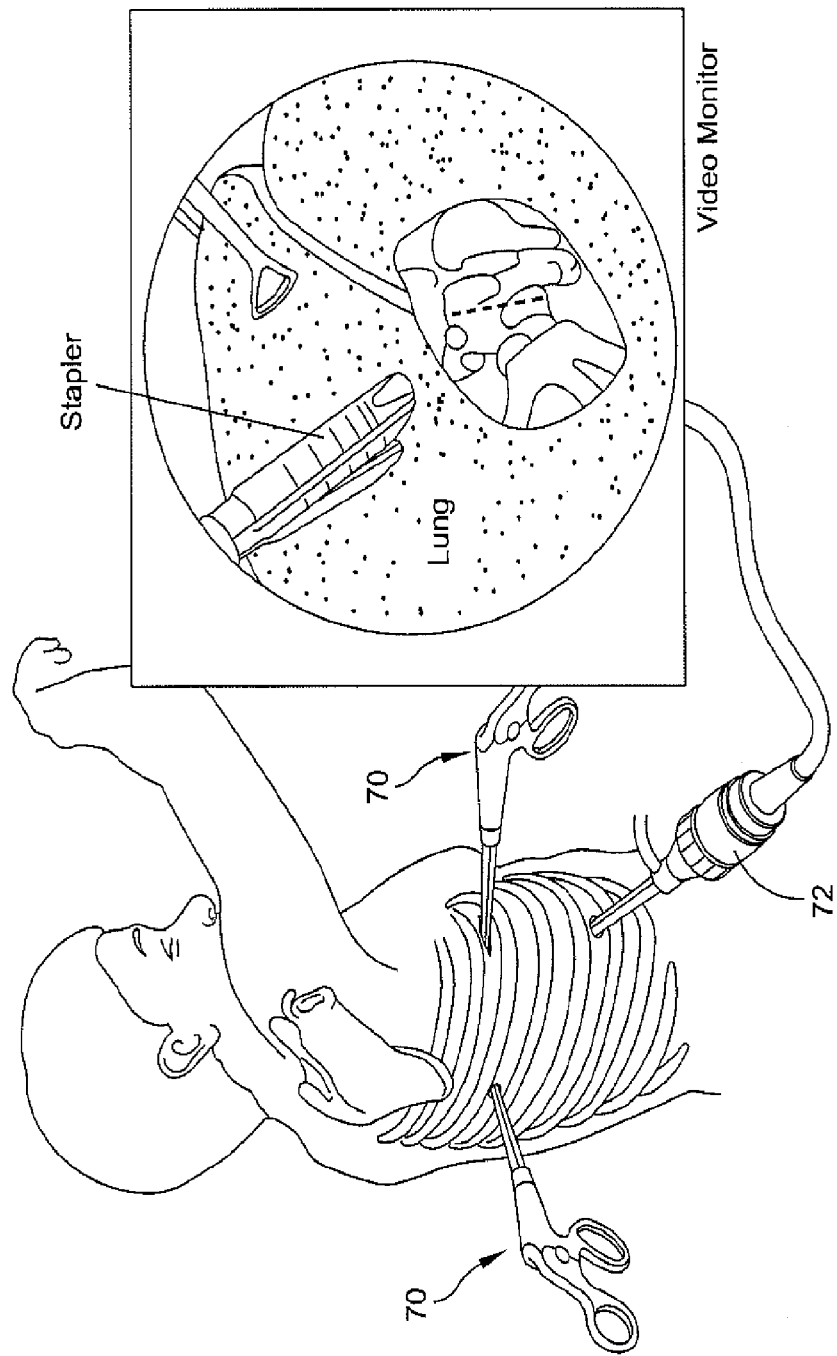
FIG. 17 schematically illustrates the use of the staple mechanism of the present invention in actual use during a surgical procedure such as a lung resection.

FIG. 9 shows still another embodiment for practicing the present invention. Instead of providing the radioactive source within the fastener or staple, in this embodiment there is schematically illustrated a series of staples 60 that may each be of conventional design but that have associated therewith a radioactive source shown at 62. The staples 60 are shown as associated with a surgical margin or incision 64. The sources 62 are distributed or positioned by means of a the line 66. In an alternate arrangement a loop may be used at 62 and the line 66 may be a radioactive line supported by the loops 62 or the line 66 may carry spaced radioactive sources. FIG. 10 schematically illustrates one standard staple array in parallel with a source array;

The concepts of the present invention are described in connection with a lung brachytherapy. In this connection reference is made to the schematic diagram of FIG. 17 illustrating a set of stapler instruments at 70 that are each respectively engaged through a skin incision. This is illustrated in FIG. 17 as between ribs. FIG. 17 also illustrates the conventional video thoracoscope at 72 introduced through another incision for viewing the operative site. As indicated previously, this particular procedure is described herein in connection with a lung wedge resection. In this regard refer to our previously issued U.S. Pat. No. 7,604,586, the complete contents of which are now hereby incorporated by reference herein.

Before discussing the particular stapler construction of the present invention, reference is now made to FIG. 10 for an illustration of the staple patterns. This includes a first pattern of three rows of standard staples at 74. This array of standard staples at 74 is disposed along the cut tissue edge 78. The lung tissue is internal as at 76 in FIG. 10. The source staples are also illustrated in FIG. 10 at 75 in a row of two parallel arranged sets of staples. It is noted that the staple array 75 is substantially in parallel to the staple array 74. To provide optimum brachytherapy application, it is noted that the source array 75 is closest to the lung tissue 76.

Figure 11:
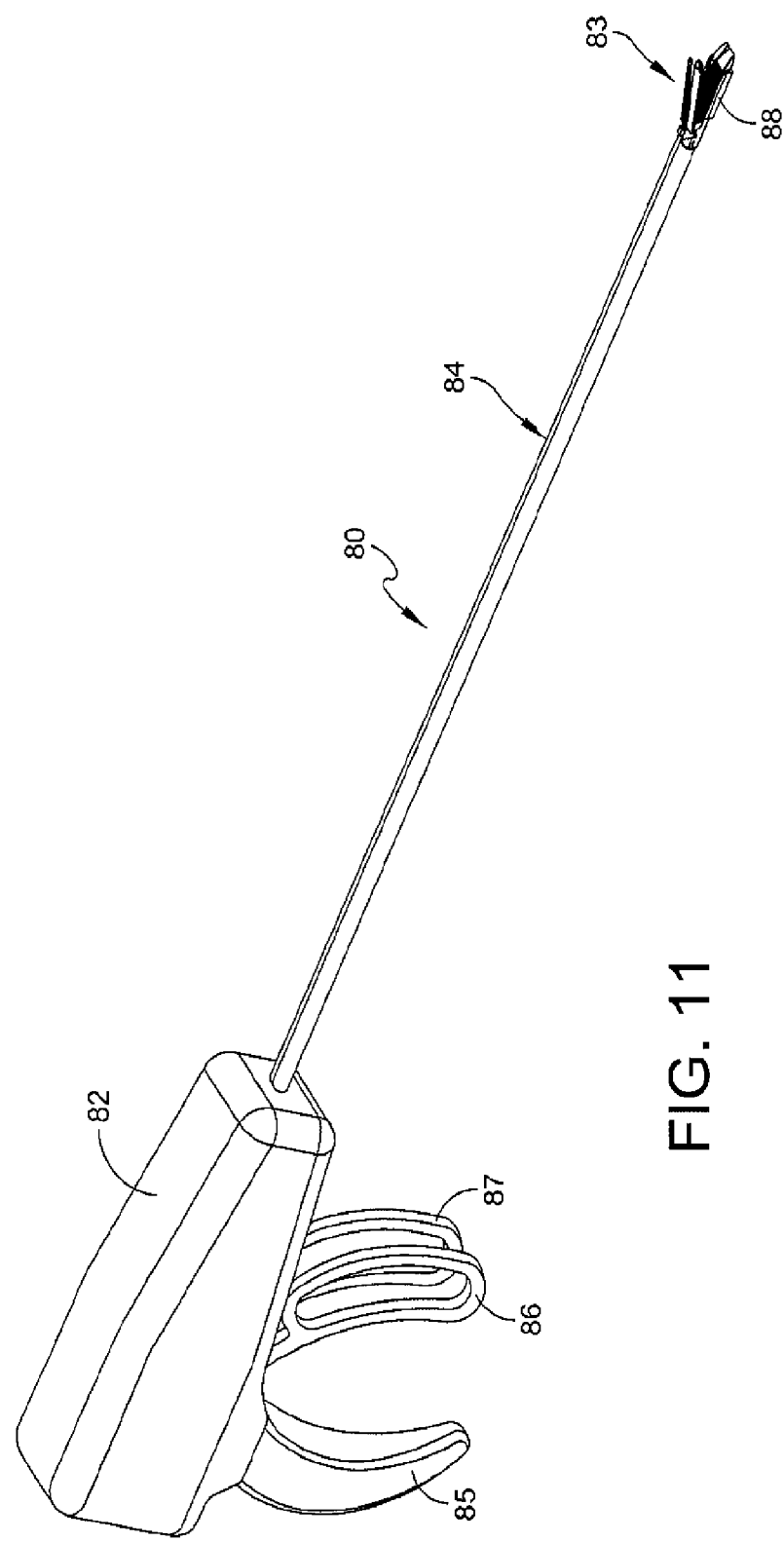
FIG. 11 is a perspective view depicting an instrument constructed in accordance with the principles of the present invention and illustrating side-by-side staple mechanisms; one for applying standard staples and the other for applying source staples.

Reference is now made to a surgical stapling instrument 80 illustrated in FIG. 11 as in accordance with the present invention. This source delivery system is used in conjunction with a standard surgical stapling apparatus. By integrating a permanent brachytherapy source in association with a standard surgical stapling instrument, there is provided a single instrument that can cut and seal lung tissue and simultaneously place a permanent radioactive seed implant. In the description, even though reference is made to a procedure relating to a lung resection, it is noted that the principles of the present invention may be applied to any one of a variety of different surgical procedures. The instrument 80 in FIG. 11 illustrates this dual purpose use in a single instrument.

In FIG. 11 the instrument 80 is comprised of a handle body 82 with a fixed handle 85 and a pair of staple cartridge actuators 86 and 87. The body 82 is coupled by means of the instrument shaft 84 to the end effector 83. FIG. 11 also illustrates a holder 88 for retaining the two separate staple cartridges described in further detail in FIGS. 12-16. Basically, these devices operate on the basis of having a proximal actuator, such as the actuators 86 and 87 in FIG. 11 herein, operate distal staple application mechanisms which typically include a cartridge of staples. One of these packages holds standard staples while the other cartridge holds source staples adjacent thereto.

Figure 12:
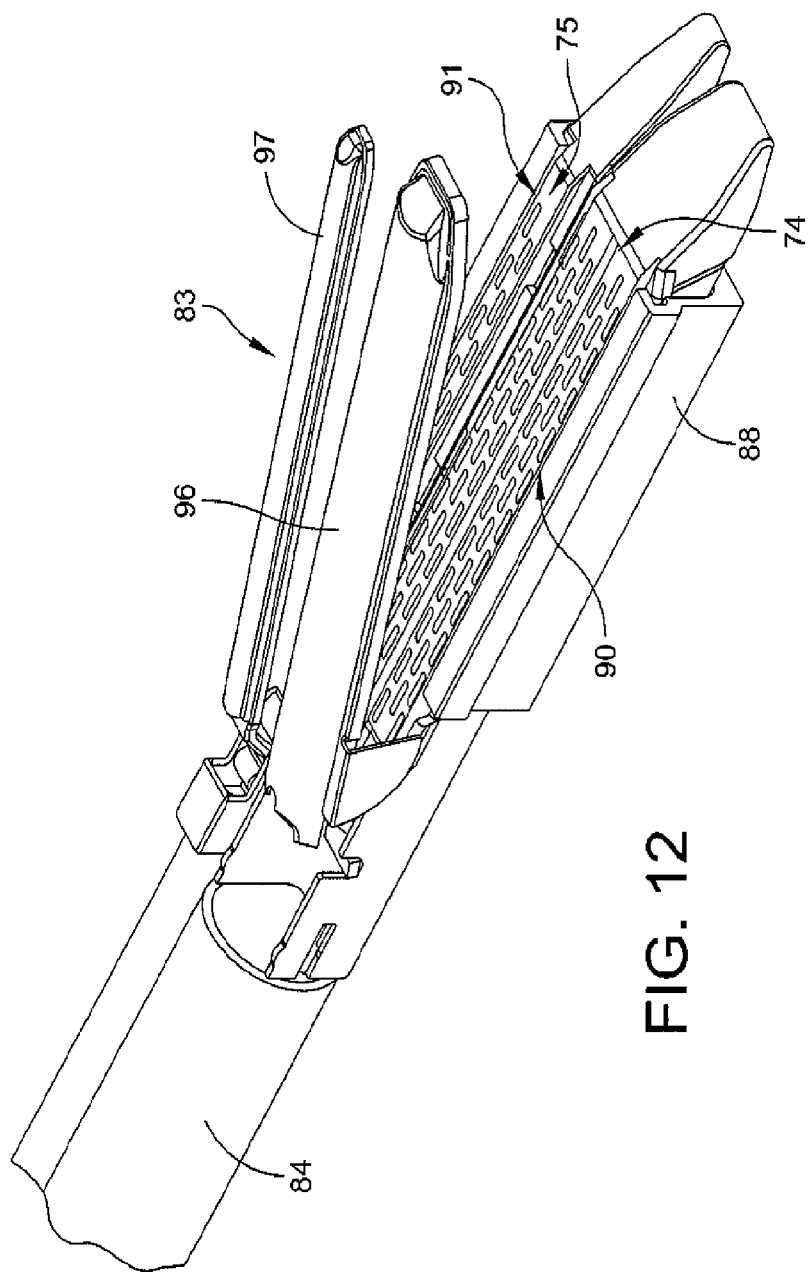
FIG. 12 is an enlarged fragmentary perspective view at the distal end of the instrument with the staple mechanisms retained by a common holder.

FIG. 12 is a perspective view at the very distal end of the staple instrument with the end effector 83 being comprised of separate but commonly held (holder 88) staple mechanisms 90 and 91. Associated with the staple mechanism 90 is actuator arm 96 and associated with the staple mechanism 91 is the actuation arm 97. In further connection with FIG. 11, the actuation lever 86 operates the actuation arm 96 and separately the actuation lever 87 operates the actuation arm 97. Each of the staple mechanisms 90 and 91 may be comprised of a body and a cartridge that holds multiple staples. These staples are illustrated in, for example, FIGS. 12-14. The standard staples are shown at 74 and the source staples at 75. In this particular instrument, there are side-by-side arrays of two sets of standard staples. Each set includes three rows of staples. For the source staples, there are two parallel rows of staples. In addition to the actuator arms 96 and 97, there are typically provided associated anvils (not shown) for closing each of the staples. Further details of these stapling mechanisms are found in the aforementioned U.S. patents which are hereby incorporated by reference herein. FIG. 12 illustrates the side-by-side arrangement of the stapler mechanisms 90 and 91 held within the holder 88. Refer also to the perspective view of FIG. 15 which shows the holder 88 having a channel 94 for receiving the mechanism 90 and a channel 95 for receiving the mechanism 91. In the perspective view of FIG. 12, it is noted that the standard staple array is disposed on the inner side of the source staple array. In another arrangement, and depending upon the particular surgical procedure, these arrays may be alternated in position so that the standard staple array is outside of the source staple array. The relative placement between these two arrays is a function of the desired side that the source staples are being placed in relationship to the standard surgical staples.

Figure 13:
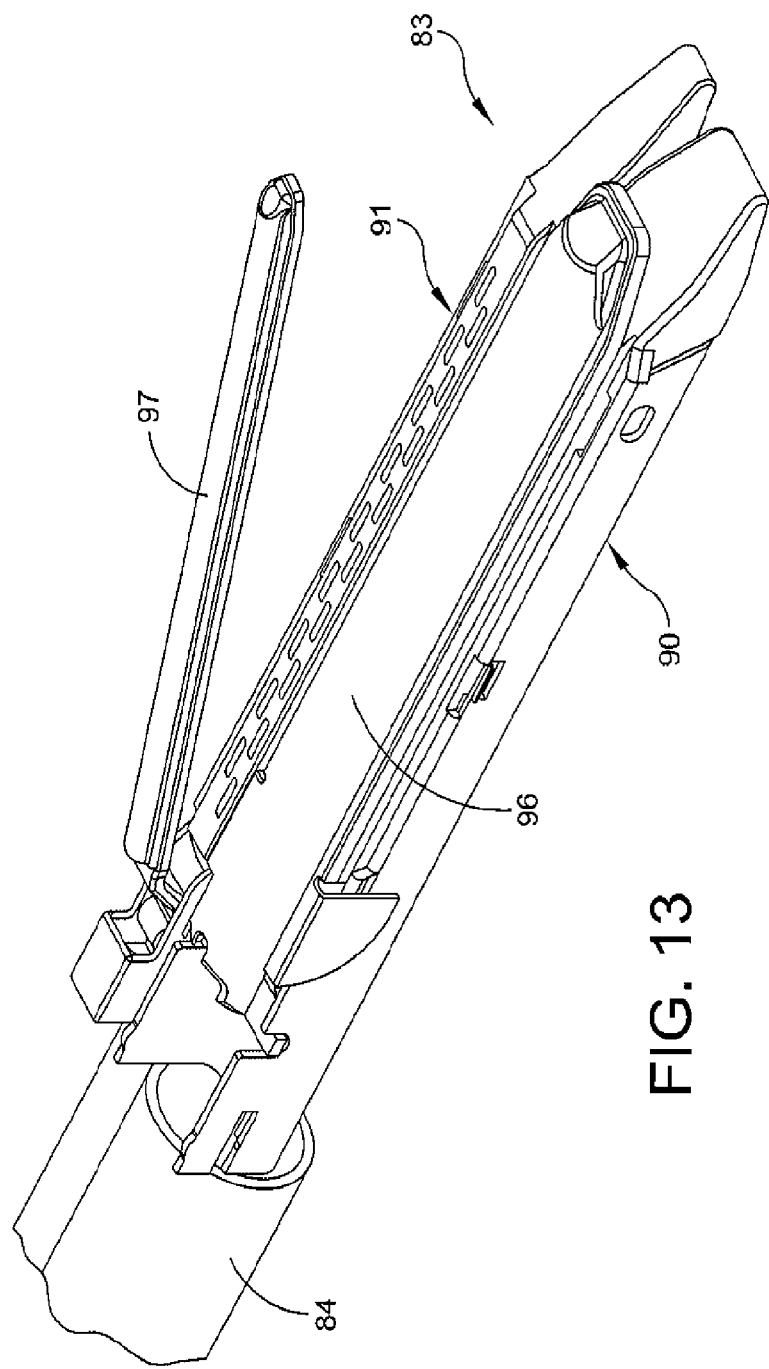
FIG. 13 is an enlarged fragmentary perspective view at the distal end of the instrument with the standard staple mechanism actuated.
Figure 14:
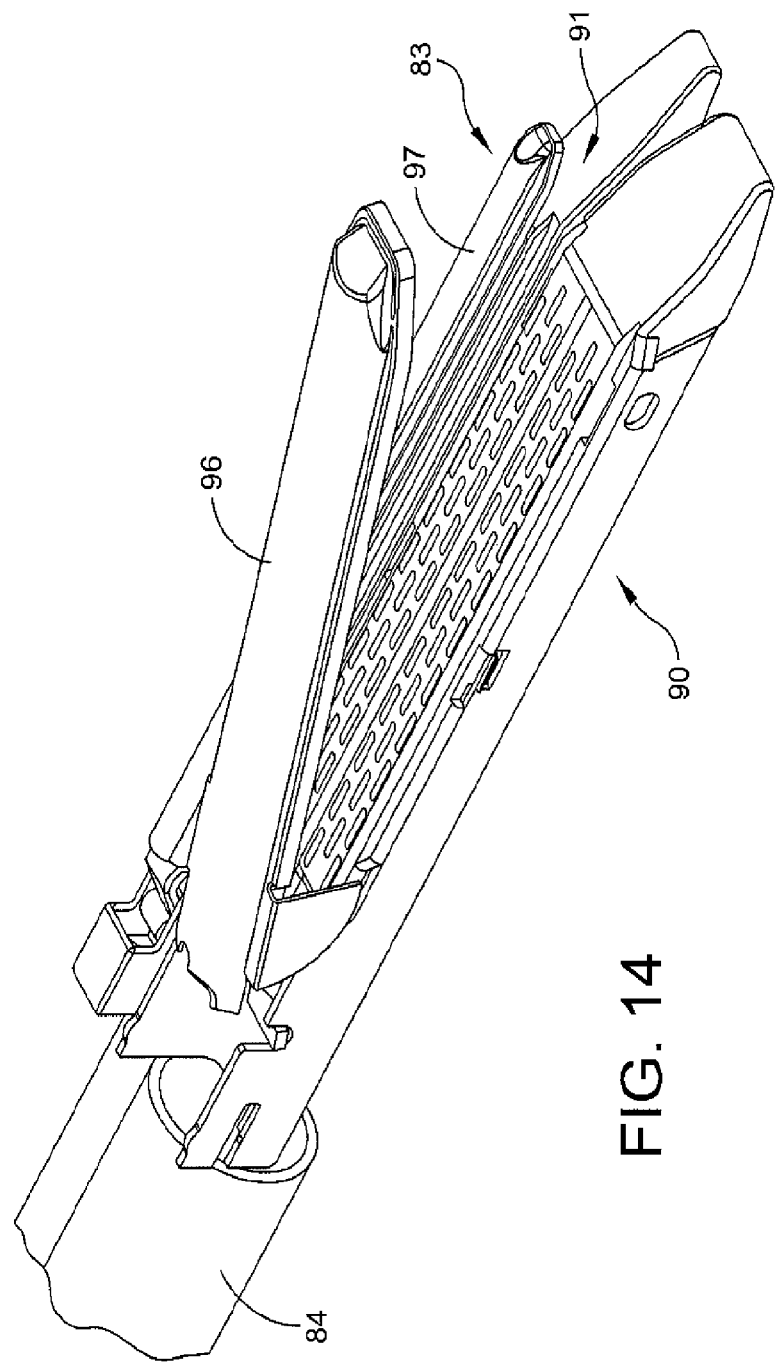
FIG. 14 is an enlarged fragmentary perspective view at the distal end of the instrument with the source staple mechanism actuated.
Figure 15:
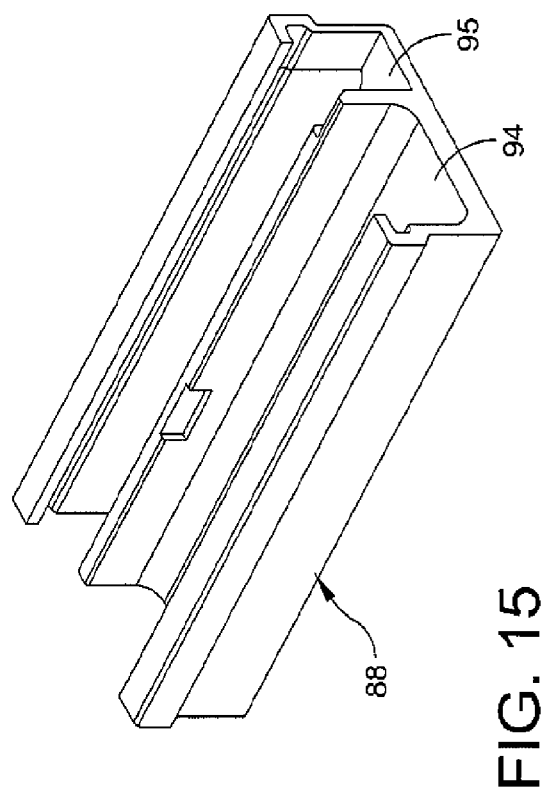
FIG. 15 is a perspective view of the staple mechanism holder used at the distal end of the instrument.

FIG. 13 illustrates the actuation arm 96 being actuated from the actuation lever 86 for applying standard staples. Similarly, in FIG. 14 the actuation arm 97 is shown actuated from the actuation lever 87 for the application of source staples. This action provides a pattern as previously identified in FIG. 10 herein.

Figure 16:
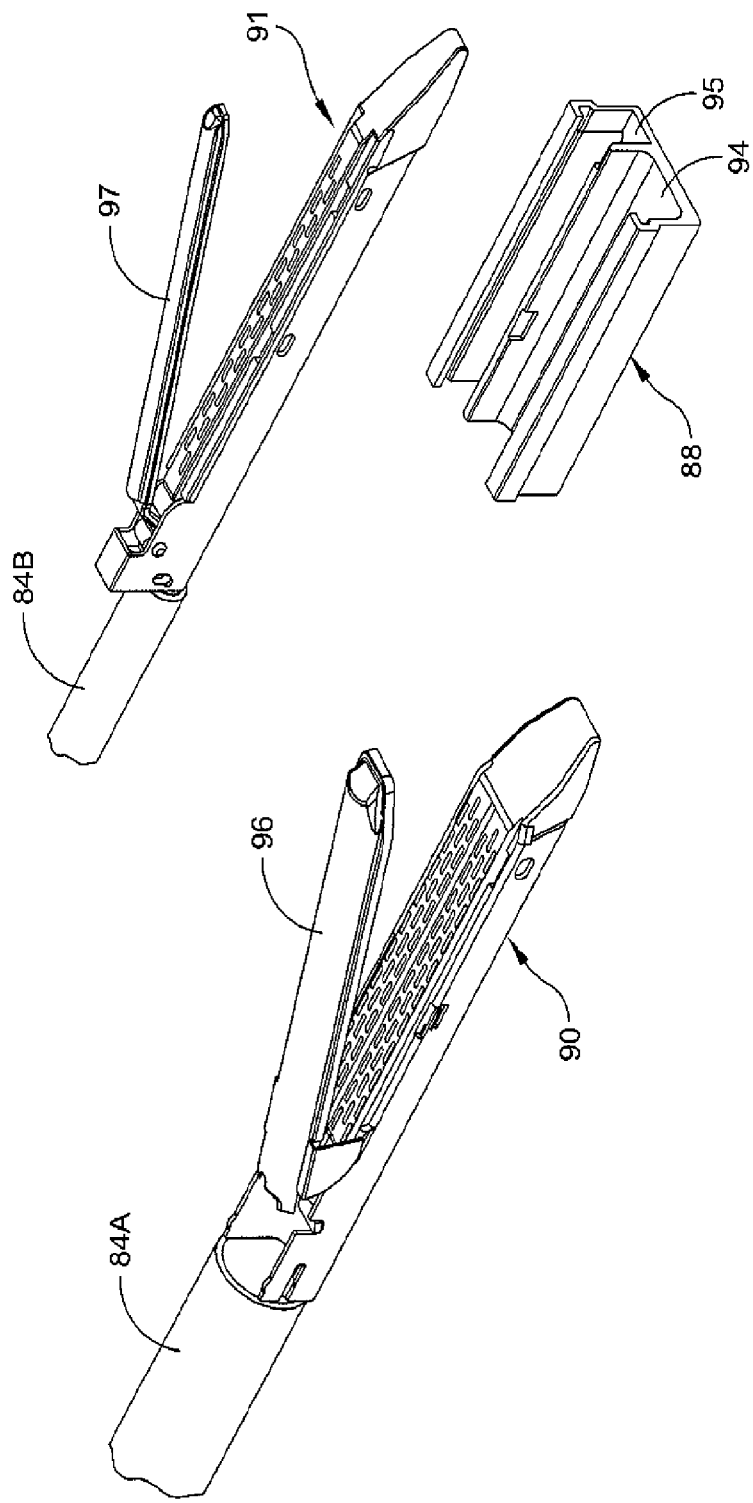
FIG. 16 is an enlarged exploded perspective view at the distal end of the instrument.

Reference is now also made to FIG. 16 that is an exploded perspective view illustrating the stapling mechanisms 90 and 91 as well as the holder 88. In FIG. 16 it is noted that there may actually be provided two separate instrument shafts 84A and 84B. These shafts typically retain a cable operated from the handle end of the instrument for controlling the respective actuator arms 96 and 97.

The stapling sequence, particularly between standard and source staples, can be performed in a number of different ways. Usually, the standard staples are first applied followed by the application of the source staples. However, it is also possible to provide concurrent lever actuation so that a source staple is applied at the same time as the standard staple. In a preferred technique, the instrument progresses along the surgical margin closing the tissue. Once a set of staples has been fastened in the pattern previously described, then the surgeon can basically progress along the same path applying the therapeutic source staples with the same basic instrument but actuating the source staple part of the end effector. Thereafter, the stapling instrument may be moved to a different location and this type of dual action repeated.

Figure 18A:
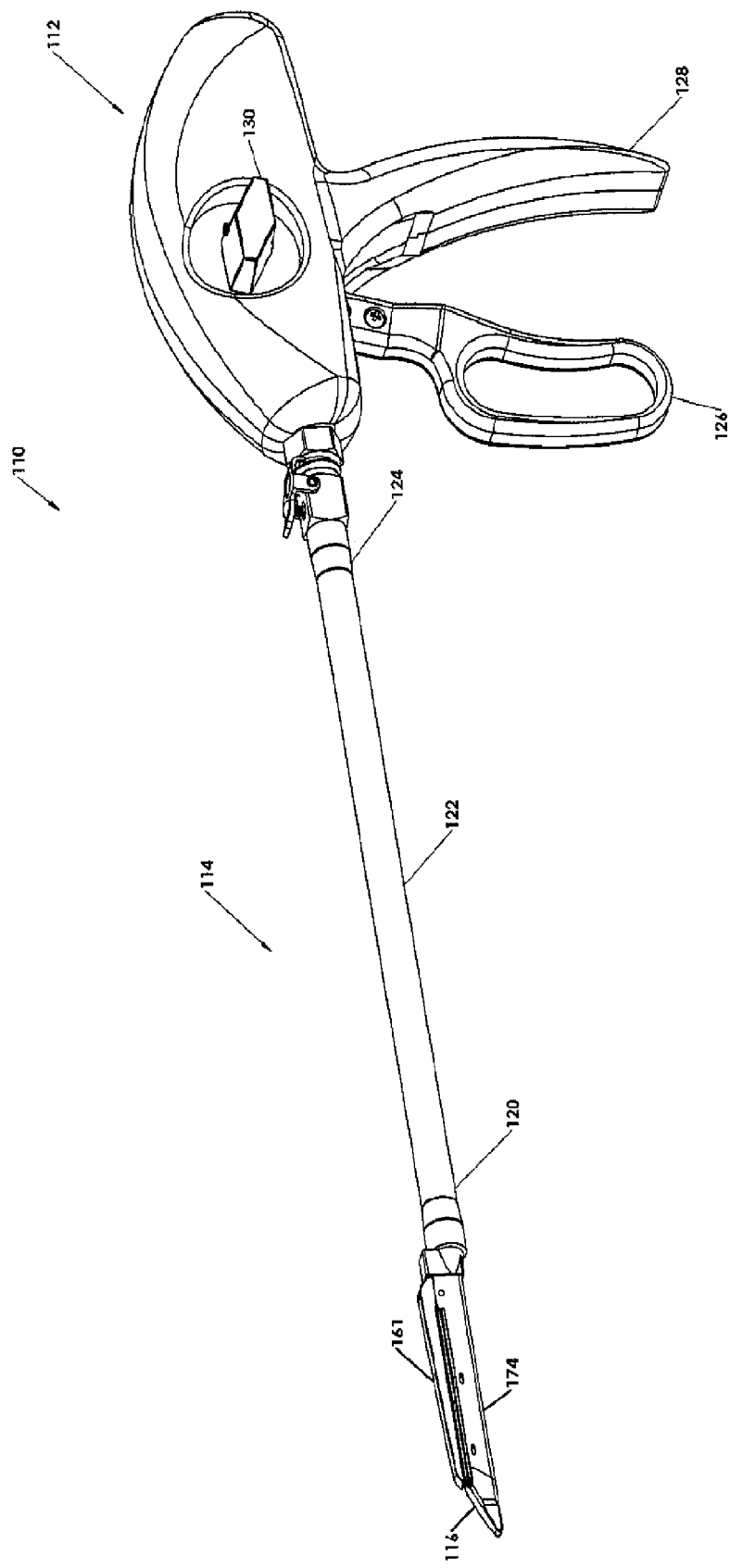
FIG. 18A is a left side perspective view of an applicator of the present invention.

The staple delivery applicator 110 is composed of a trigger device 112 and a cartridge unit 114, FIG. 18A, with a source staple cartridge 116 mounted in a cartridge holder 174. The cartridge holder 174 is mounted to a distal end 120 of an actuator arm 122 by a cartridge holder 174/actuator arm connector 207, FIG. 22A. The cable 136/sled connector 218, FIGS. 22A and 22B, allows flexible movement between the cable 136 and the sled 202 within the actuator arm 122. The actuator arm 122 is removably mounted to the trigger device 112 at a proximal end 124 by a release lever 134. The trigger device 112 has multiple controls thereon to operate the attachment of the staples, not shown. The trigger device 112 has a lever 126, a handle 128, and a release knob 130 as shown in FIG. 18A, and a toggle knob 132, FIG. 18B.

Figure 18B:
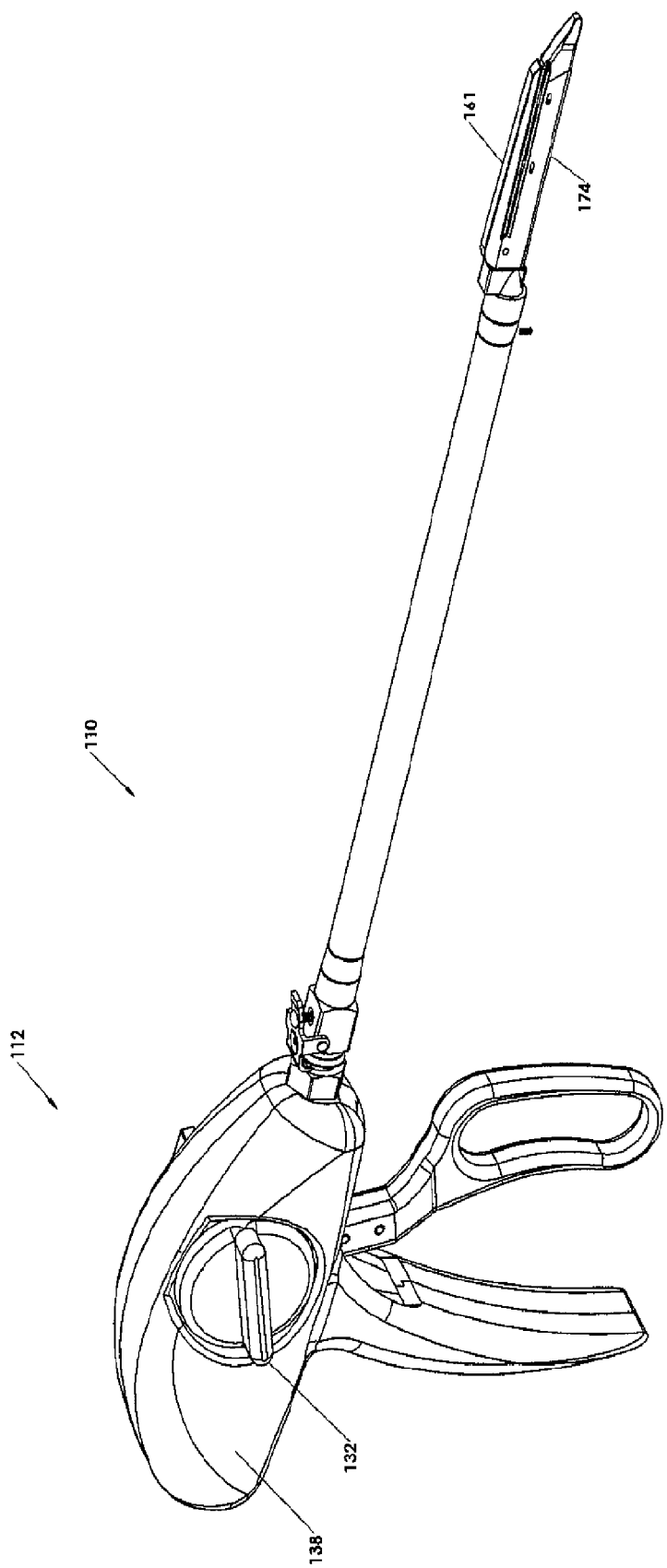
FIG. 18B is right side perspective view of the applicator of FIG. 18A.
Figure 18C:
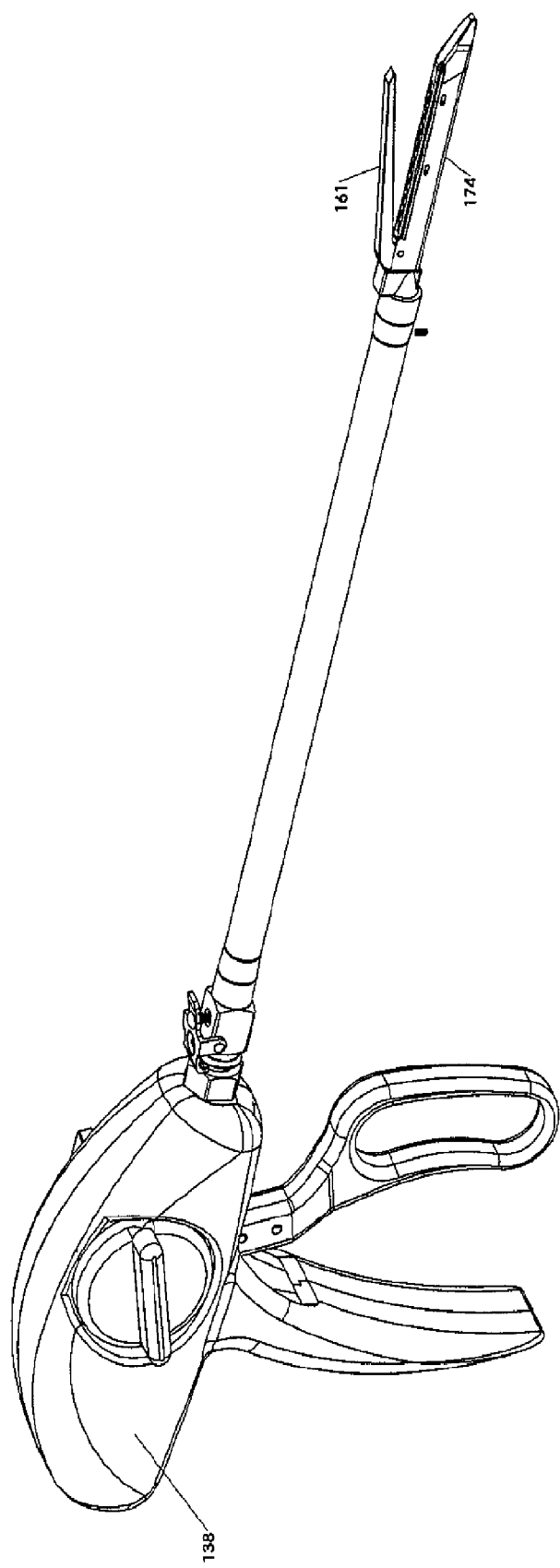
FIG. 18C is a right side perspective view of the applicator of FIG. 18B showing an anvil of a cartridge in the open position.
Figure 19:
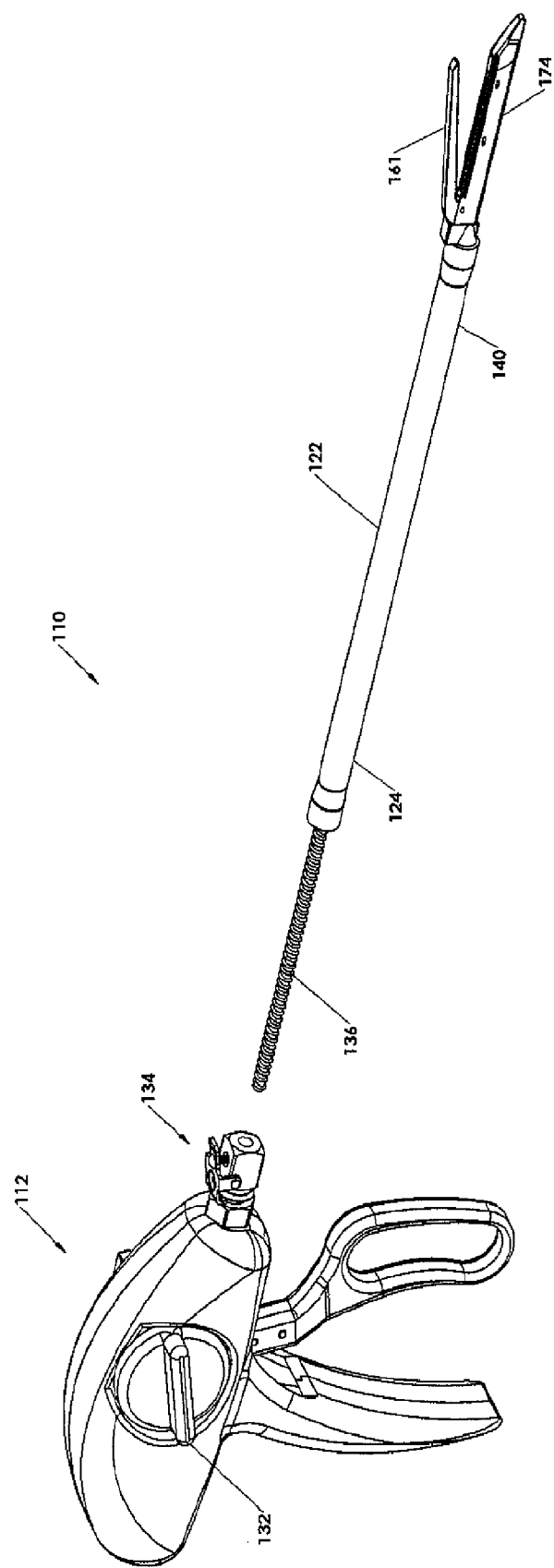
FIG. 19 is a right side view of a cartridge unit separated from a trigger of FIG. 18A of the present invention.

FIG. 18B shows the right side of the applicator 110 and the trigger 112 having the toggle knob 132 thereon. FIG. 18C shows the applicator 110 having an anvil 161 in the open position. FIG. 19 shows the actuator arm 122 removed from the trigger 112 with a cable 136 extending from a tube 140 at the proximal end 124. The spring loaded, release lever 134 allows the actuator arm 122 to be removed from the trigger 112 as needed.

Figure 20A:
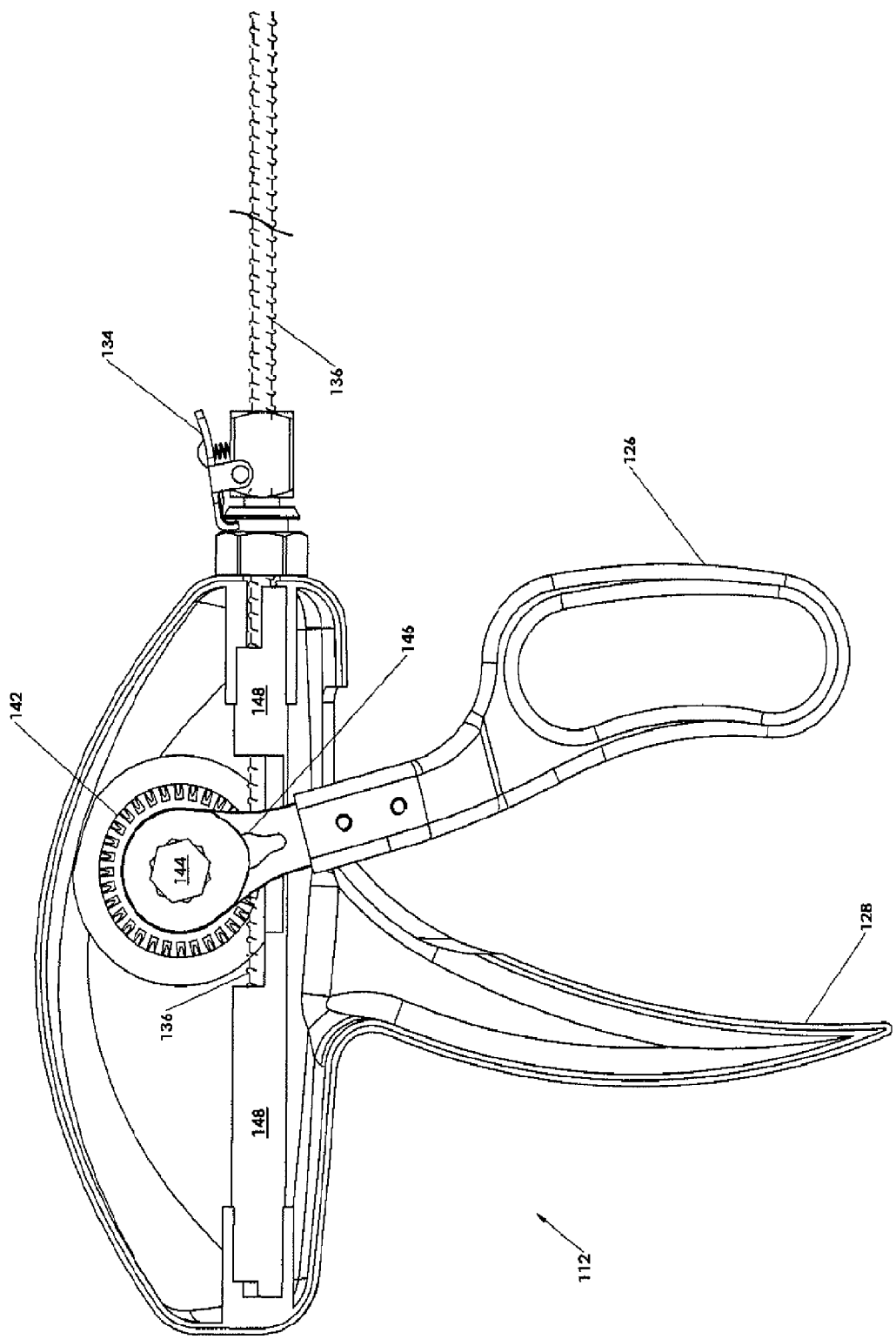
FIG. 20A is a right side view of the applicator of FIG. 18A having a right side housing removed from the trigger of the present invention.
Figure 20B:
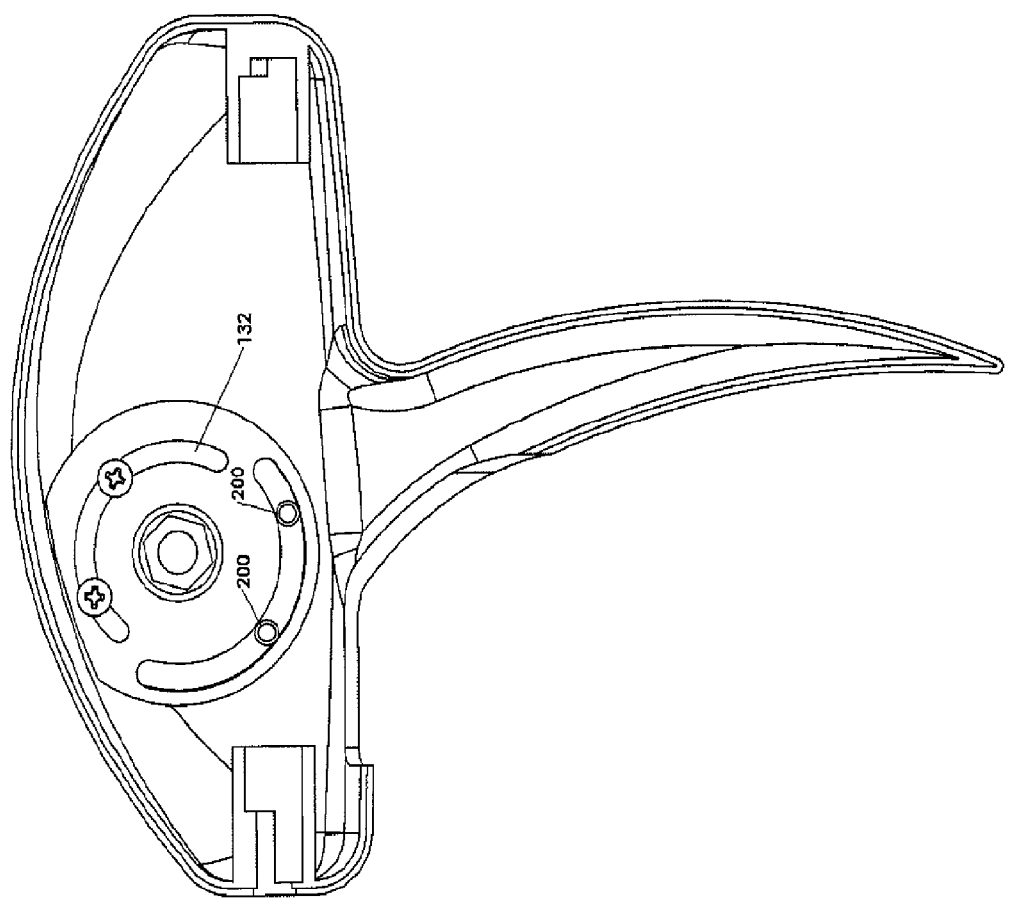
FIG. 20B is a left side view of the applicator having a left side housing removed from the trigger of the present invention, showing the back of the toggle knob on the right side of the applicator of FIG. 18B.
Figure 20C:
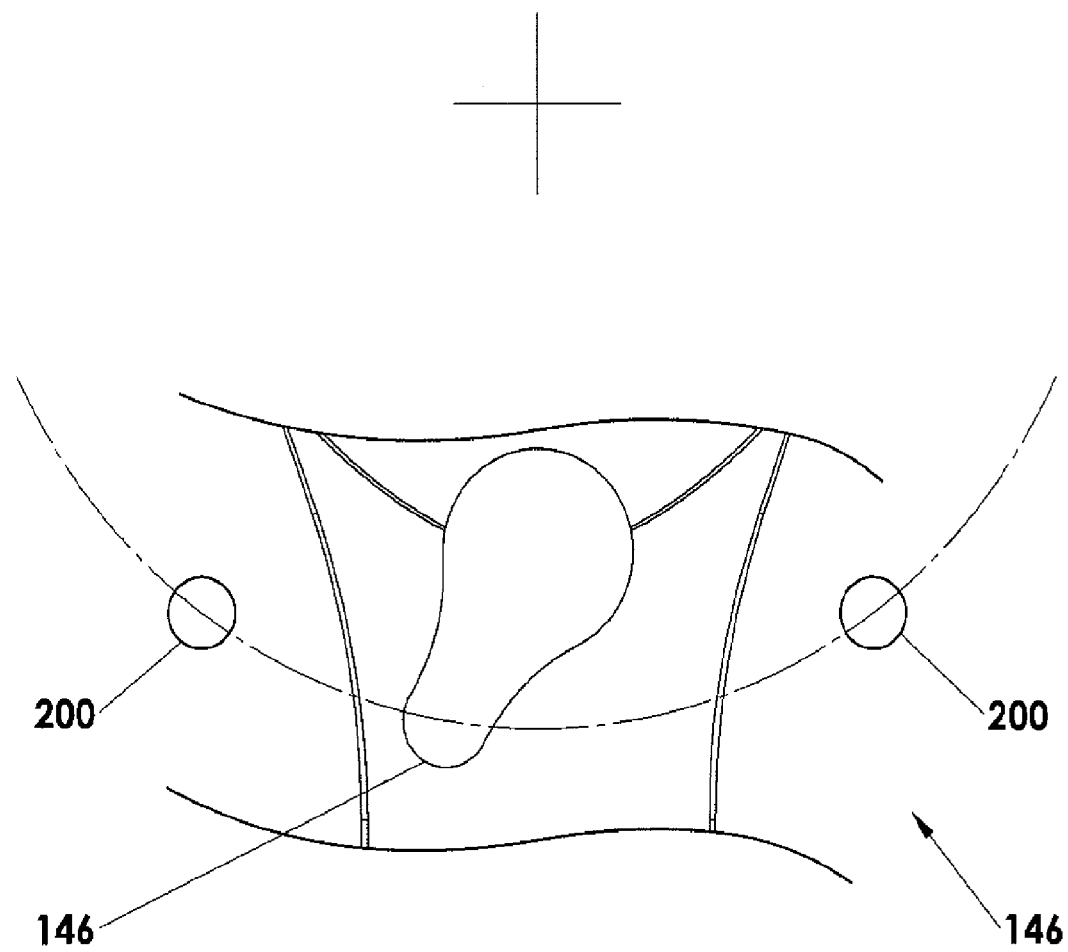
FIGS. 20C to 20D show a reverse switch mechanism that interacts with the toggle rods of the toggle knob for changing the direction of cable movement; this being one possible mechanism.
Figure 20D:
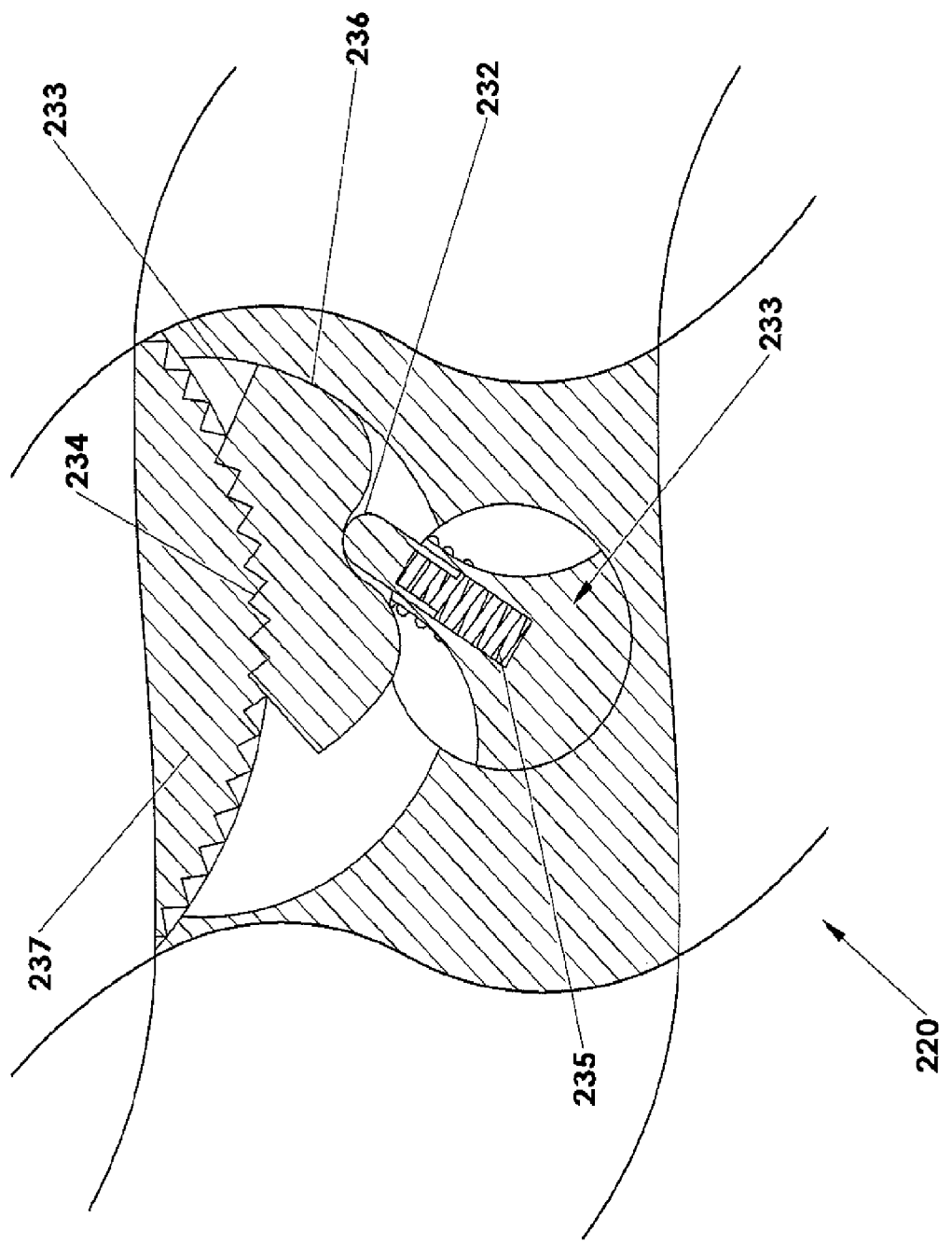

Referring to FIG. 20A, a right side housing 138 is removed from the trigger 112 to show partially the interior thereof. A gear 142 is mounted to a central shaft 144. The gear 142 translates/acts upon the cable 136 that is supported within cable guides 148. The back of the toggle knob 132, FIG. 20B, has a pair of toggle rods 200 that act upon a toggle switch 146, FIG. 20A. When the toggle switch 146 is reversed by the turning of the toggle knob 132, the release knob 130 can be then turned to translate the cable 136 out of the trigger 112 to be released. FIG. 20D shows one embodiment of a reverse switch mechanism 220. The reverse switch mechanism 220 allows the gear 142 to reverse direction such as in a wrench ratchet As shown in FIG. 20D, a reverse switch mechanism 220 is comprised of a ratchet 237, which is connected to the central shaft 144, and a pawl 233. A spring 235 biases a lever 231 to hold the pawl 233 in place. The rotating member 238 is connected to the toggle switch 146, FIG. 20C. The pair of toggle rods 200 are shown in FIG. 20C with a travel line in dashes as the toggle knob 132 is turned. In operation, if the right toggle rod 200 is turned clockwise, it will push the bottom of the toggle switch 146 clockwise to the position as shown in FIG. 20C. As a result, turning of the central shaft 144 in a counterclockwise direction is prohibited since the teeth of the ratchet and pawl are engaged 234 and the pawl hits a wall 236, preventing movement. Clockwise rotation is possible as this motion moves the ratchet 237 clockwise, pushing the pawl 233 into the lever 232 and compressing the spring 235. When the right toggle rod 200 is rotated counterclockwise, it pushes the bottom of the toggle switch 146 clockwise and the detent mechanism functions in the opposite direction. Clearly other embodiments of such a reverse switch are possible in light of the present invention and in light of the incorporated patents.

Figure 25A:
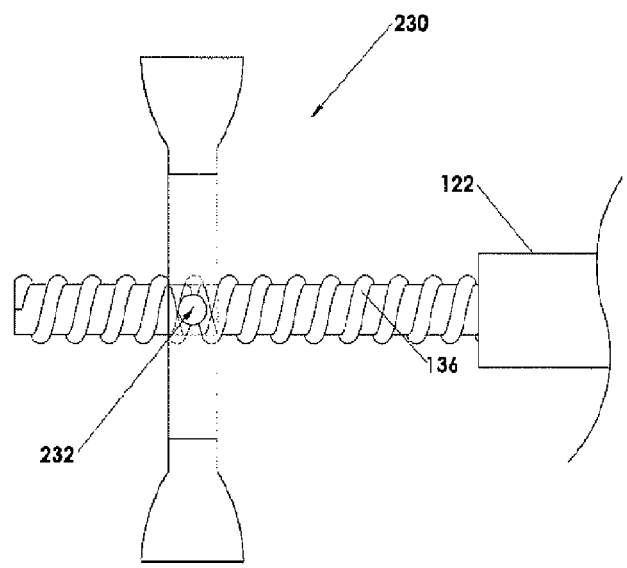
FIGS. 25A and 25B illustrate several actuating devices in addition to the trigger device as shown above for operating the cable attached to the cartridge unit.
Figure 25B:
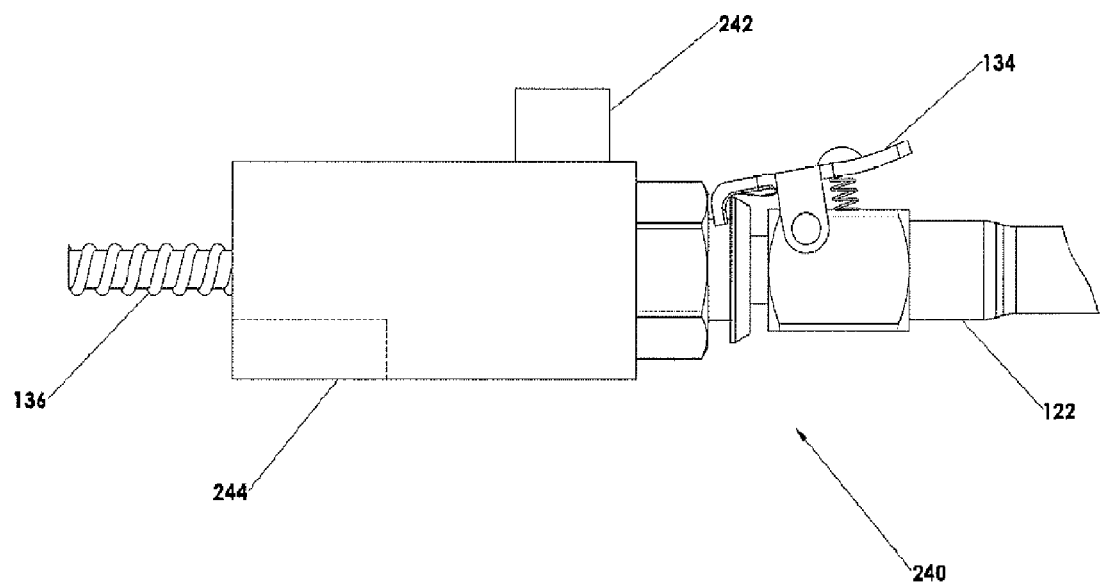

The trigger device 112 as shown above is one embodiment of an actuating means or device for operating the cable 136 in the actuating arm 122. Referring to FIGS. 25A and 25B, FIG. 25A illustrates a manual means for operating the cable 136 by attaching a handle 230 to the cable 136. It should be understood that the cable 136 has appropriate teeth thereon to engage the gear 142, but this is not required in that other actuating means may be used to move the cable 136. As shown, the handle 230 is attached to the cable 136 that extends from the actuating arm 122. The cable 136 is secured in the handle 230 by a locking means 232. The operator would then grasp the handle 230 and the tube 140 of the actuating arm 122 and move the cable 136 as desired and in a manner consistent with the movement noted above. Another embodiment of the actuating means is shown in FIG. 25B that is an electric actuating means 240 that is connected onto the actuating arm 122 by a release lever 134 such as shown on the trigger device 112. A power source 244 such as batteries or an external source provides power to a reversible electric motor 242 that is geared to mesh with the cable 136. A forward or reverse switch 246 is used to control the movement of the cable 136 within the actuating arm 122.

Figure 21A:
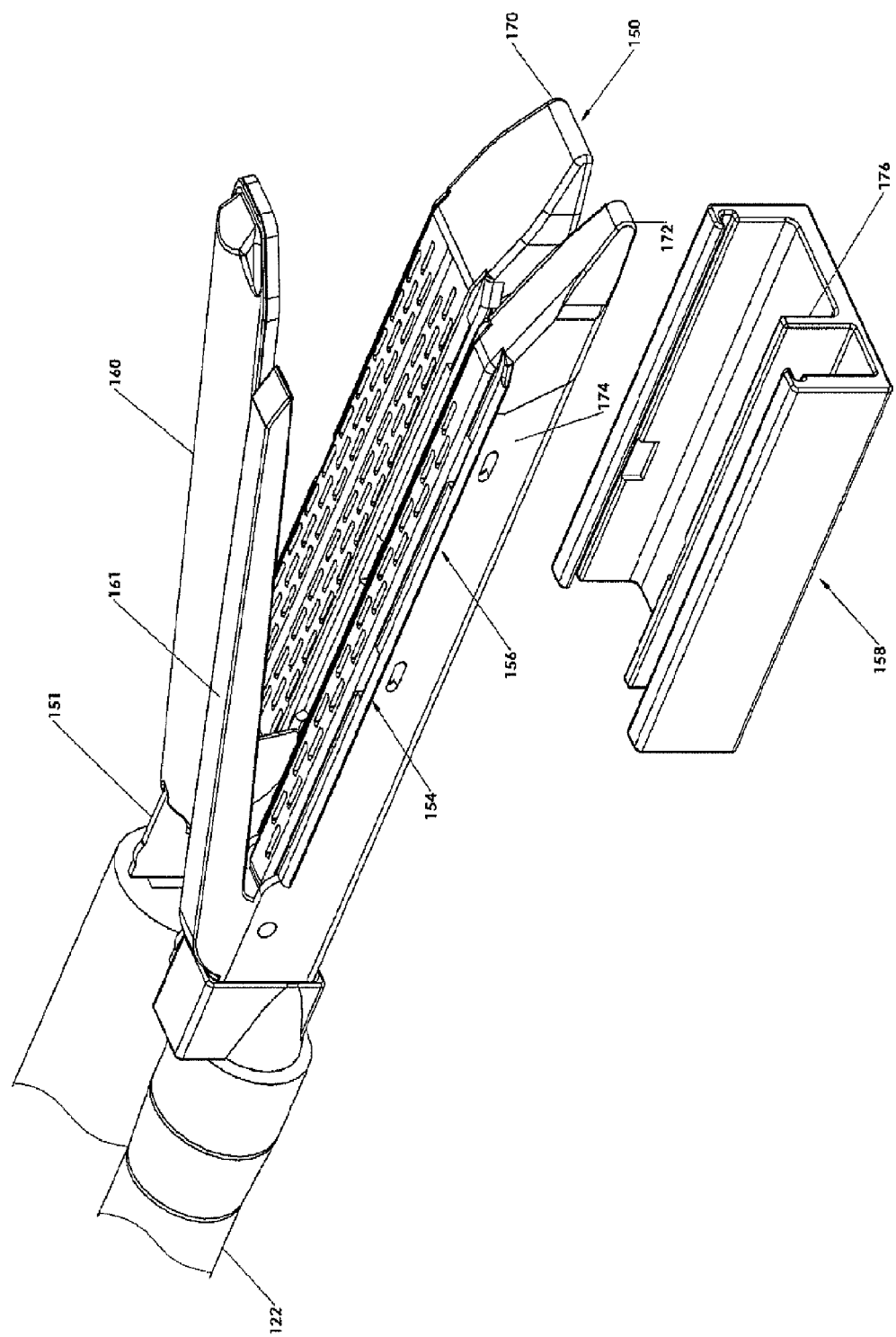
FIG. 21A is a partial perspective view of the cartridge unit of FIG. 19 along side of a surgical staple cartridge with a connector located below in the present invention.
Figure 22A:
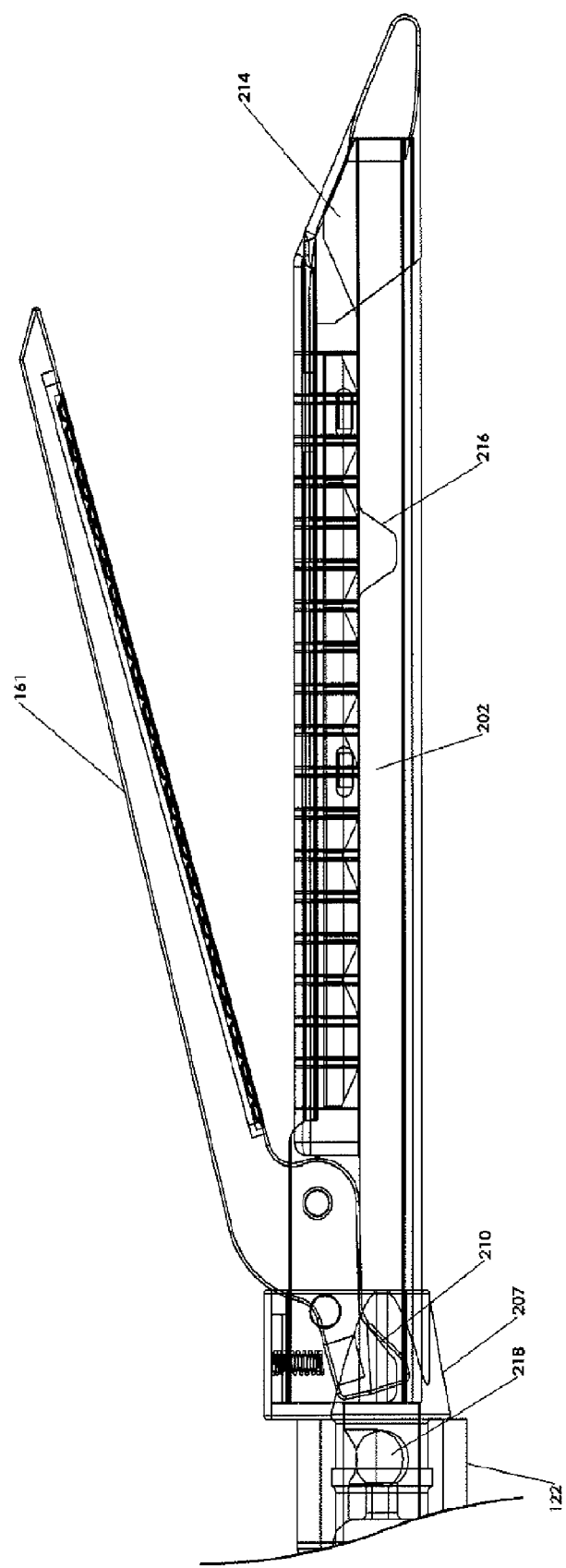
FIG. 22A is a partial side view of the cartridge unit of FIG. 19 with the anvil open showing by x-ray view an inside of the cartridge unit of the present invention.
Figure 22B:
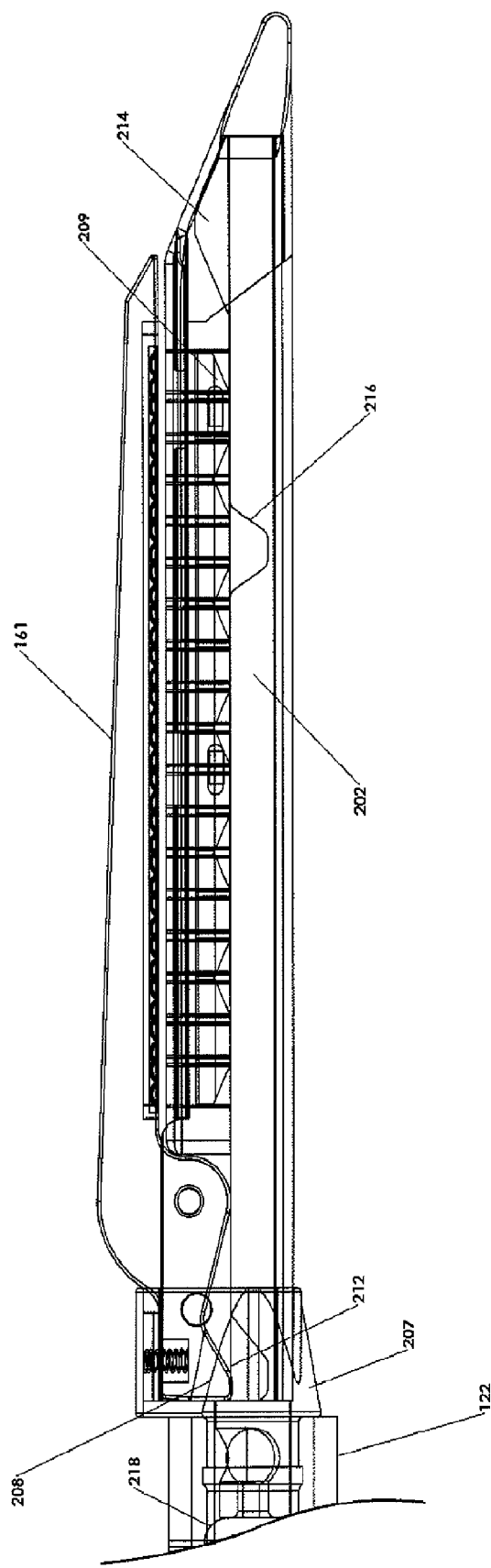
FIG. 22B shows the anvil closed as compared to FIG. 22A of the present invention.
Figure 23A:
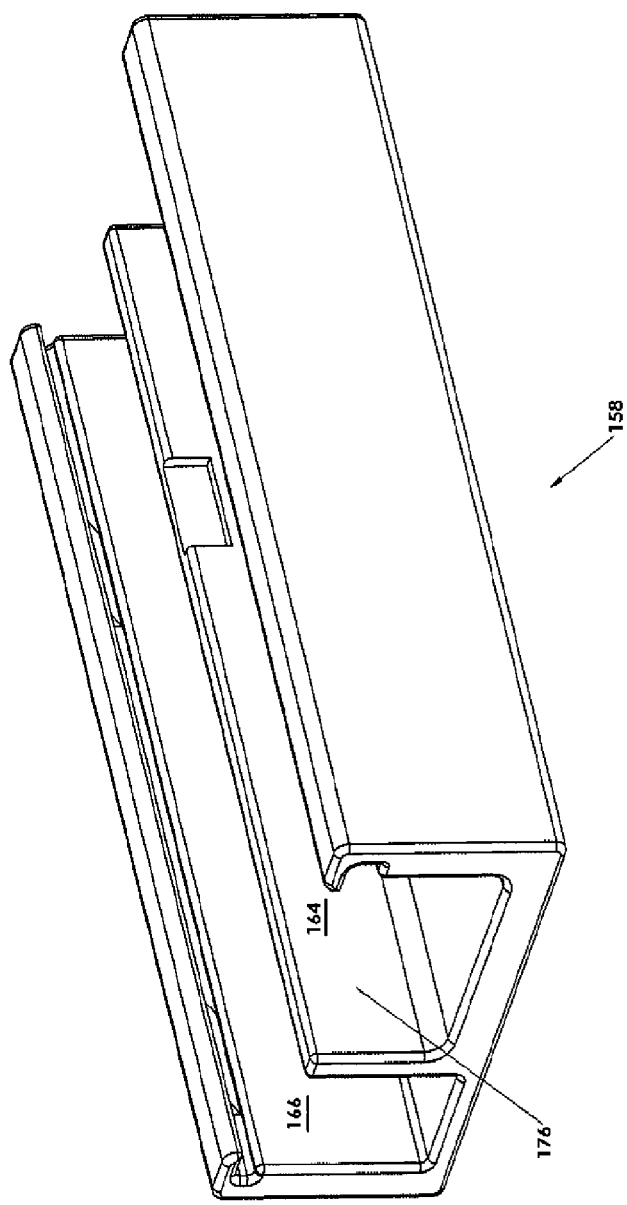
FIGS. 23A to 23D shows by perspective views one embodiment of the connector of the present invention.
Figure 23B:
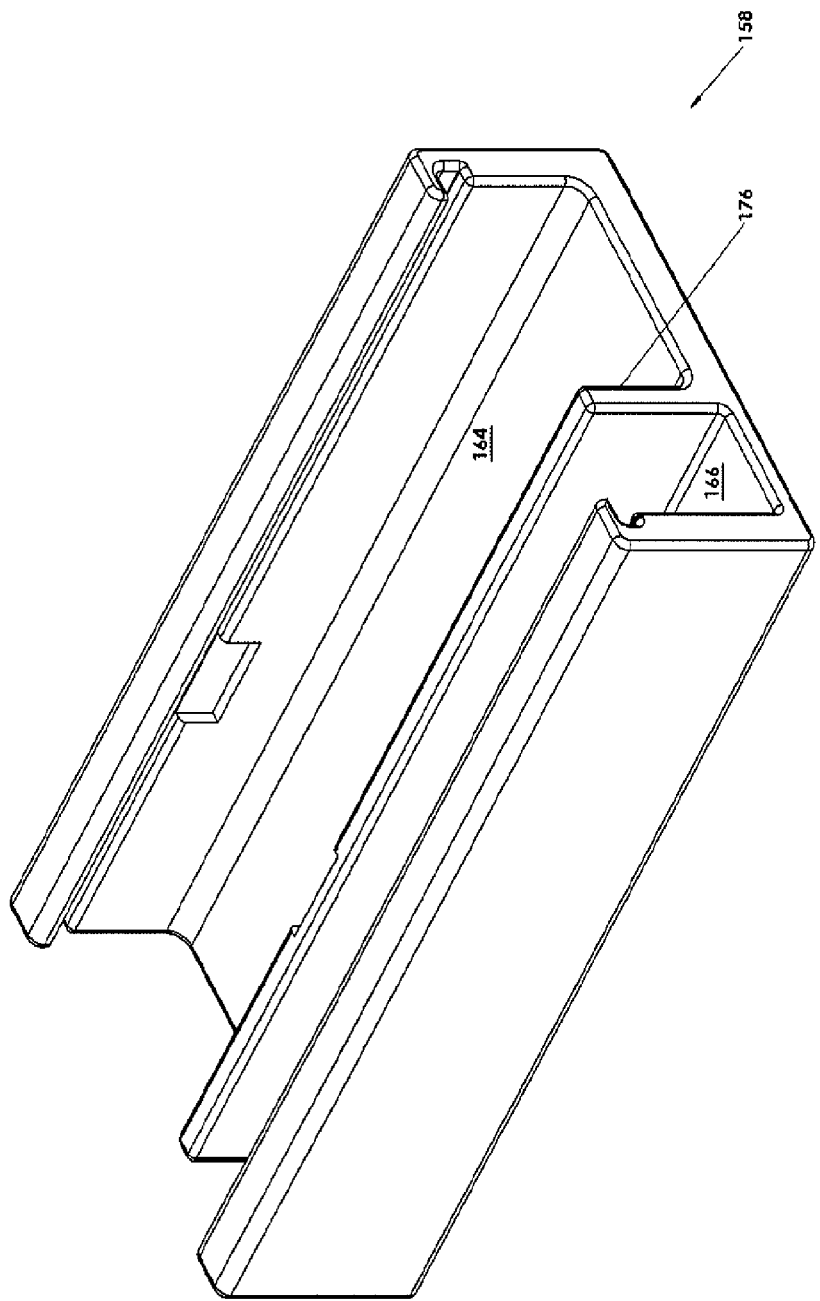
Figure 23C:
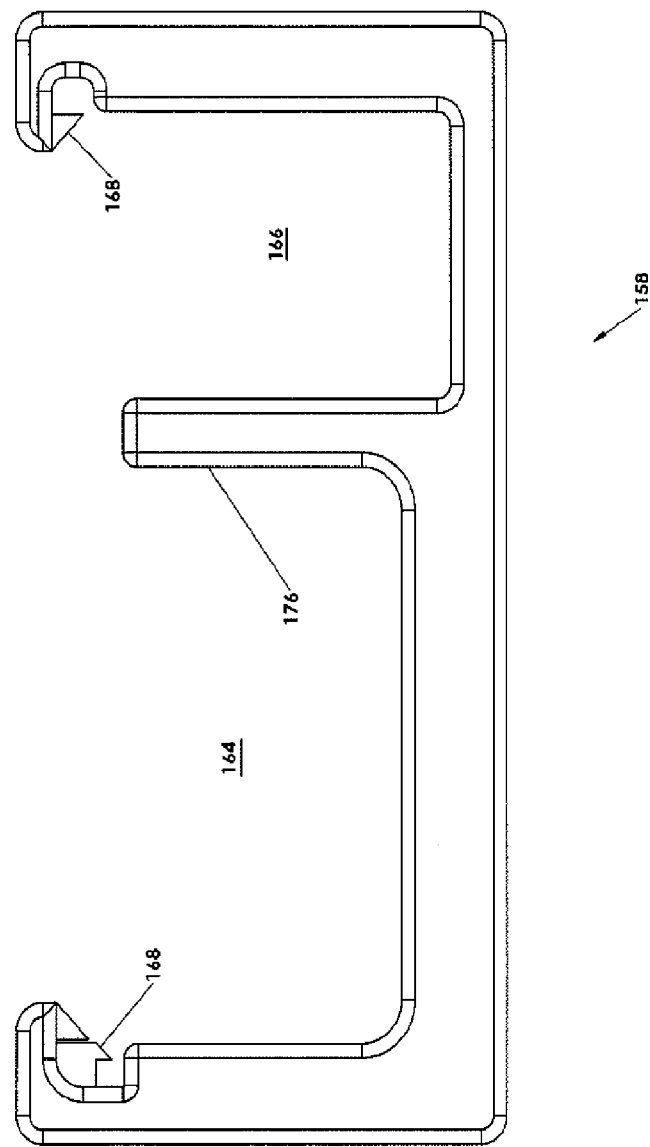
Figure 23D:
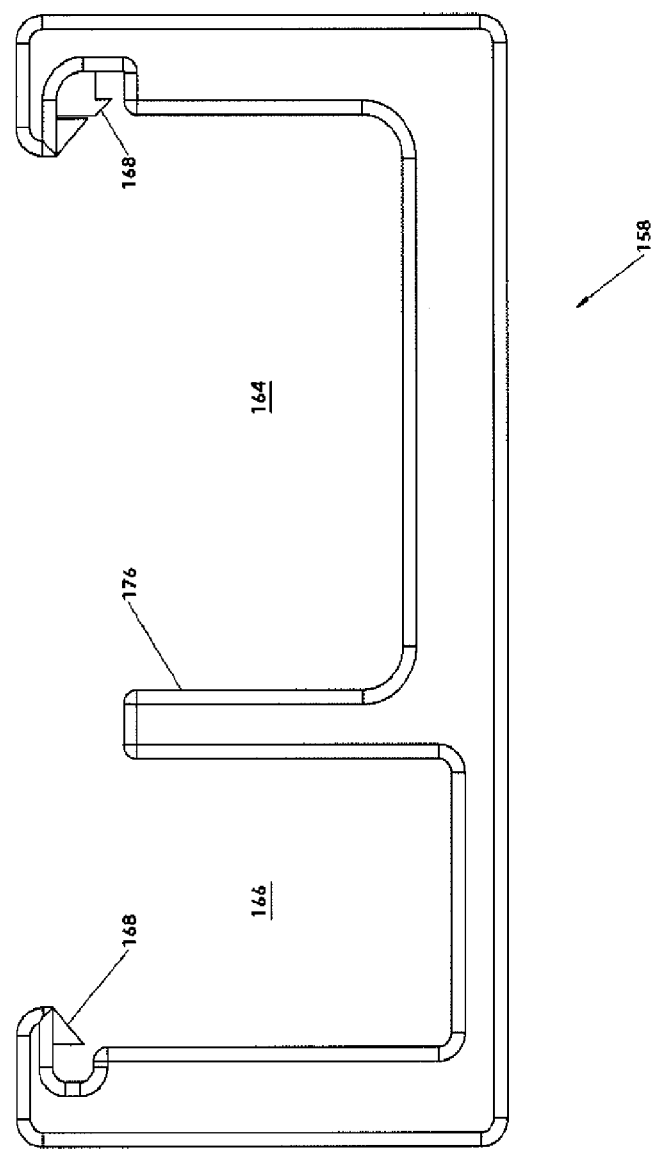

To better understand the operation of the applicator 110, FIGS. 18A, 20A, and 21A, the source cartridge 152 is loaded into the source cartridge holder 174. With the cartridge 152 in place, the actuator sled 202, FIGS. 22A and 22B, is pushed toward the proximal end of the cartridge holder 174 and into the proximal end of the anvil 161 and causes the source anvil 161 to open as shown in FIG. 22A. The source anvil 161 is a part of the source staple cartridge holder 174 and is pivoted at a pivot 204. An upper spring 206 forces an end 208 of the source anvil 161 into a first detent 210 to open. As the attached cable 136 is slightly retracted, the end 208 rides up an inclined groove to a top 212 of the actuator sled 202 and closes the anvil 161, FIG. 22B. Further pulling of the lever 126 in a clockwise direction to further retract the cable 136 causes a sled hammer 214 to push up on the bottom of inclined pushers 209 that push up on the bottom of the source staples therein crimping them. After the crimping is completed, the end 208 falls into a second detent 216 in the sled 202 and then opens the anvil 161. The source cartridge 152 then can be removed. At that point, the cable 136 is fully retracted. In order to reverse the cable 136 movement in direction, at any time, the toggle knob 132 is rotated to cause the toggle rods 200, FIG. 20B, to change the position of the reverse switch 146. Then, the release knob 130 is rotated to push the cable 136 back and the actuator sled 202 back into the cartridge holder 174. The toggle knob 132 must then be reset to its initial setting so that the cable 136 can be retracted. Manual operation of the applicator 110 may be obtained by allowing the cable 136 to extend from a rear of the trigger 112 with the attachment of a handle thereon. The handle can be pulled to retract the cable 136 and pushed in to return the cable 136. The toggle knob 132 would have to be also appropriately turned in the manual operation.

Figure 21B:
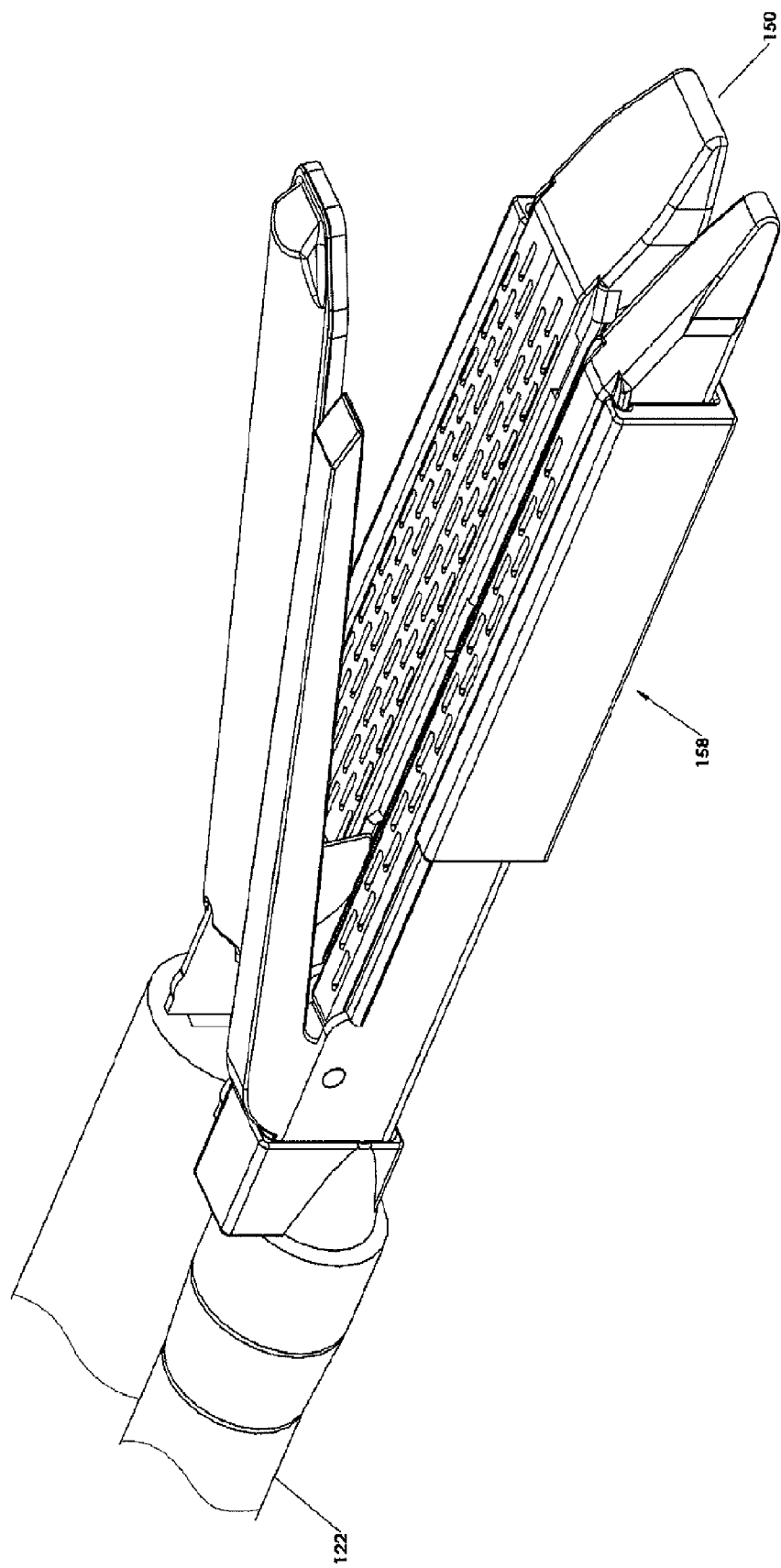
FIG. 21B is a partial perspective view as in FIG. 21A but showing the connector installed on the cartridges.

In one embodiment as best shown in FIGS. 21A and 21B, the delivery applicator 110 may be attached in a parallel manner to an existing surgical staple device 150 such as disclosed in U.S. Pat. No. 7,494,039. The applicator 110 may also be positioned in a parallel manner next to the surgical stapler cartridge as shown in FIG. 21B. The applicator cartridge 152 contains radioactive sources/staples, not shown (see U.S. Pat. No. 7,604,586 showing radioactive staples which is incorporated by reference) in predetermined positions 154: two rows with staggered slots 156, FIG. 21A. Other configurations of the slots 56 are clearly appropriate and would be designed based upon the medical need for such. There may be a standard set of slots such as shown in FIG. 21A, but the source staples could be placed therein as desired. After deployment of the conventional surgical staples, not shown also, the applicator staples would be independently deployed by use of the trigger 112 immediately adjacent to the surgical staples. The fixed relationship by use of a connector 158 on the applicator cartridge 152 to the surgical staple cartridge 150 assures an accurate fixed position of the source/staples relative to the surgical staples, and therefore the surgical resection margin created by the surgical staple device having a cutting means therein.

Currently, surgical staples are delivered by a wedge-shaped driving element within the cartridge which presses a piston through the cartridge cavity causing the staples to be pressed against an anvil 160 causing the staple legs to be bent over within an anvil bending device such as seen in a common stapler.

The applicator cartridge holder 174 is attached to either the right-hand or left-hand side of the surgical stapler cartridge 150 so as to be useful on either leg/side of a typical wedge resection. Source positioning will not be restricted to the typical "1-centimeter" spacing that is currently used. The ability to have closer source positioning, especially at the ends of the line of sources, will afford the opportunity to differentially load the cartridge (i.e. have greater activity at the ends) to compensate for the dose "drop-off" typical of such an array of sources/seeds.

One embodiment of the present invention has a one-piece connector 158, FIGS. 23A to 23D and FIGS. 21A and 22B, for holding both the conventional surgical staple cartridge 150 and the applicator cartridge 152 in parallel alignment so that the radioactive applicator staples can be applied directly along side of the conventional staples. This provides accurate placement of the radioactive applicator staples near possible cancerous tissues. The other embodiment of the connector is a modular connector 162, FIGS. 24A and 24B, for holding the applicator cartridge 152, which is connected to the conventional staple cartridge 150 also being held in the modular connector 162.

The staple delivery applicator 110 may use the connector 158, FIGS. 23A to 23D, being the one-piece connector 158 having two parallel channels 164 and 166 for holding the applicator cartridge 152 in channel 166 and the conventional staple cartridge 150 in the channel 164 such as shown in FIG. 21B. Sets of tabs 168, FIGS. 23C and 23D, in each channel align the cartridge holder 174 to detentes thereon wherein the front ends 170, 172, FIG. 21A, of each of the cartridges align. FIGS. 23A to 23D show the one-piece connector 158 in various views. This one-piece connector 158 may fit upon the carrier portion 250 as mentioned and shown in patent '039 above in FIG. 19. It should be noted that the surgical staple cartridge channel 164 is wider than the source/staple cartridge channel 166 since there are 6 slot rows in the surgical staple cartridge 150 as compared to 2 in the source cartridge 152. Further, the width of a separating wall 176 may be varied based on medical requirements. The connector 158 is typically made of plastic and further may include radiation shielding material. The cartridges 150 and 152 are mounted in cartridge holders 174 and 151 that are then pushed into the channels 164/166. The applicator holder 174 is connected to the actuator arm 122 as to the present invention.

Figure 24A:
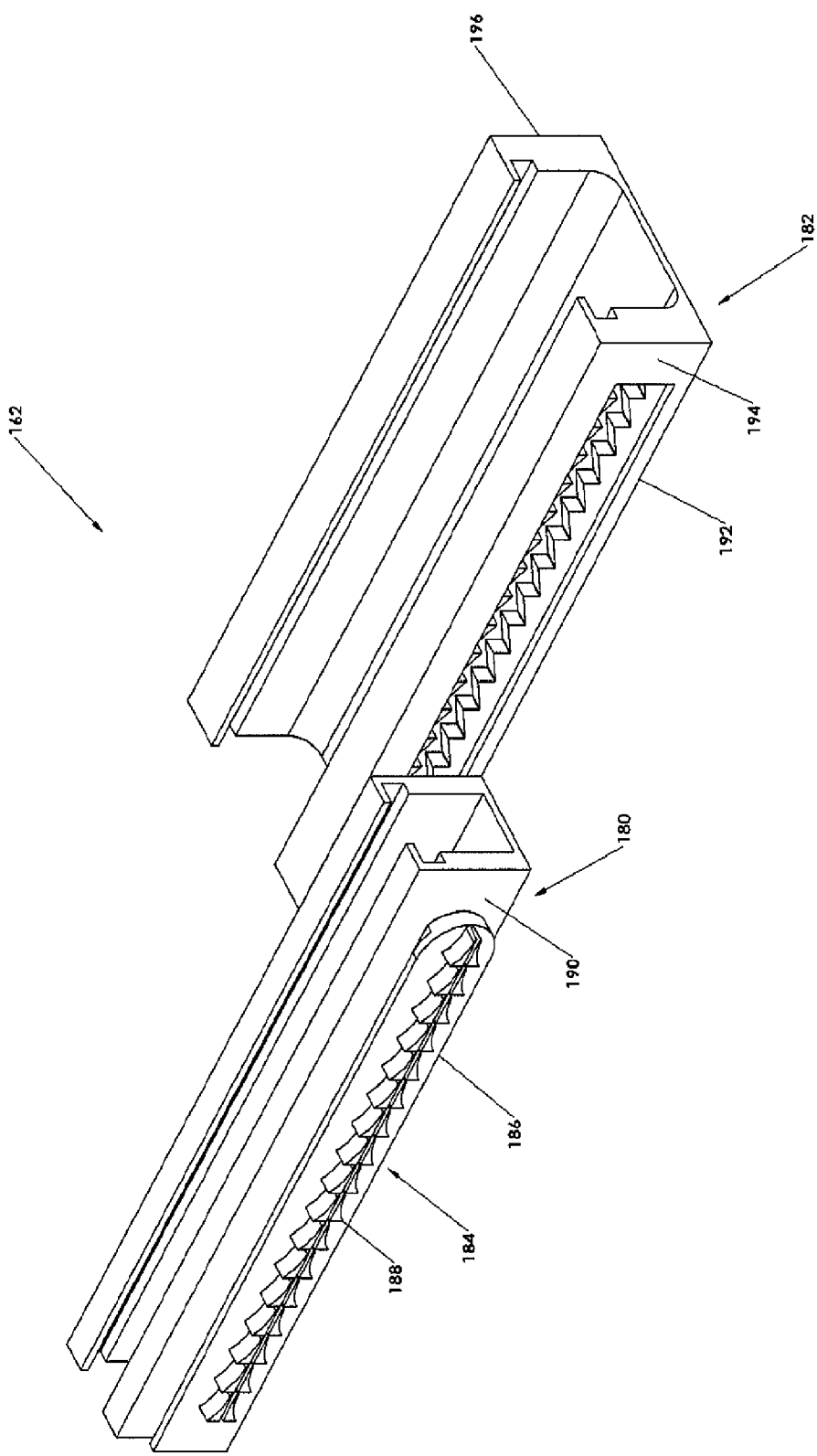
FIGS. 24A to 24B shows by perspective views the embodiment of both modular units being installed together.
Figure 24B:
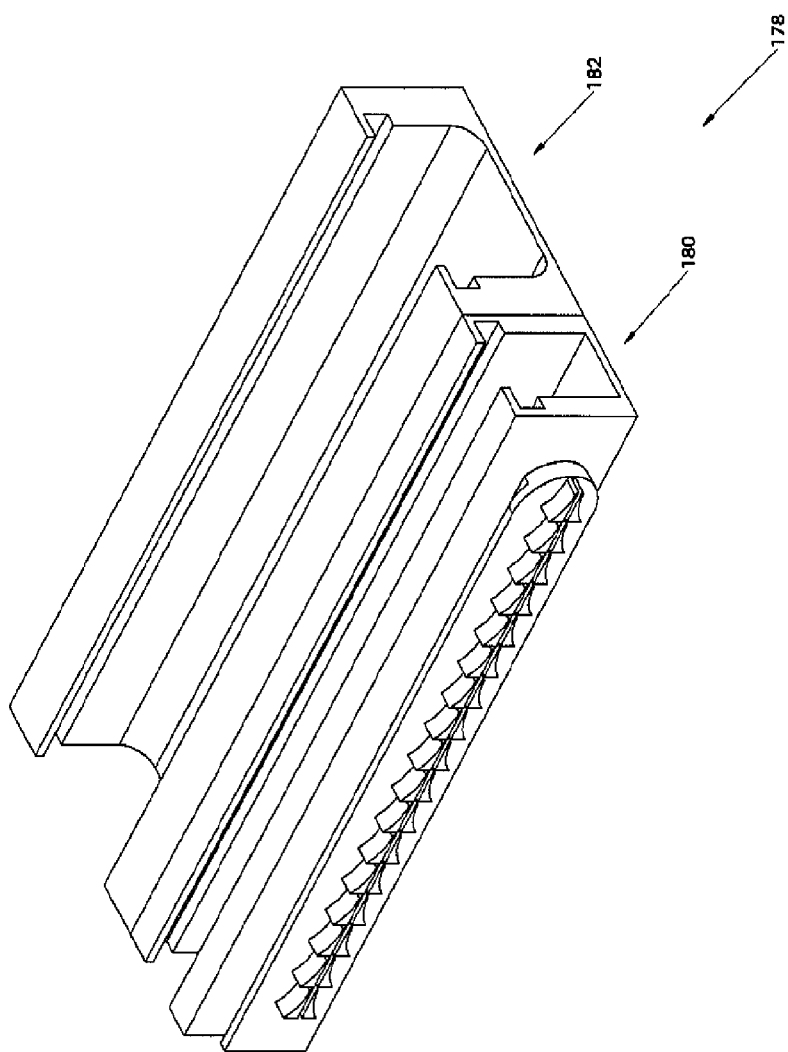

The modular applicator connector 178 is shown in FIGS. 24A and 24B. FIG. 24A shows the modular applicator connector 180 being inserted/connected/mounted to one side of a staple device connector 182. The applicator connector 180 may be attached to either side of the staple device connector 182. FIG. 24A shows one portion of a male attachment 184 having a row 186 of flexible triangles 188 mounted on the applicator connector 180 vertical side 190. The other portion of a female attachment 192 being the complement of the male attachment 184 is shown. Both sides 194, 196 of the staple device connector 182 have the female attachments 192 so that the applicator connector 180 may be mounted to either side as required during surgery. The modular connector 178 in FIG. 24B shows the applicator connector 180 fully inserted onto the device connector 182.

The staple delivery applicator 110 further includes radiation shielding in either the staple cartridge 152 itself or on the applicator connector 158, preferably in the applicator cartridge 152 since the radioactive staples would be mounted there. The shielding material may be a part of the composition of the cartridge 152 or be a layer of shielding mounted thereabout. The anvil 161 of the cartridge unit 114 may also be shielded to fully prevent exposure from radiation to the operators of the staple applicator 110. The shielding would minimize the radiation dose to the physician deploying the device as well as to the other personnel in the operating room. The shielding will permit safe storage of this device in the Operating Room until it is time for use. The device will also be designed for sterilization, and resterilization, using steam, ethylene oxide and gamma radiation to provide total flexibility to the hospital.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

Having now described a limited number of embodiments of the present invention, it should be apparent to those skilled in the art that numerous embodiments and modifications thereof are contemplated as falling within the scope of the present invention as defined by the appended claims.

[i] Jemal, Siegel, et al. "Cancer Statistics, 2009." CA Cancer J Clin. 2009; 59:225-249.

[ii] American College of Surgeons. "National Cancer Database for 2003." <http://www.facs.org/cancer/ncdb/index.html>.

[iii] Ginsberg, R. J. and L. V. Rubinstein. "Randomized Trial of Lobectomy Versus Limited Resection for T1 N0 Non-Small Cell Lung Cancer." Lung Cancer Study Group Ann Thorac Surg. 1995 Sep.; 60 (3): 615-22. <K"http://ats.ctsnetjournals.org/cgi/content/full/60/3/615"http://ats.ctsnetjournals.org/cqi/content/full/60/3/615>.

[iv] Martini, Bains, et al. "Incidence of Local Recurrence and Second Primary Tumors in Resected Stage I Lung Cancer." J Thorac Cardiovasc Surg. 1995 January; 109(1): 120-9

[v] Ichinose, Yano, et al. "The Correlation Between Tumor Size and Lymphatic Vessel Invasion in Resected Peripheral Stage I Non-Small-Cell Lung Cancer." A potential risk of limited resection. J Thorac Cardiovasc Surg. 1994 October; 108(4):684-6.

[vi] Choi, N. C. "Prospective Prediction of Postradiotherapy Pulmonary Function With Regional Pulmonary Function Data: Promise and Pitfalls." Int J Radiat Oncol Biol Phys. 1988 July; 15(1):245-7.

[vii] Ginsberg, R. J. and L. V. Rubinstein. "Randomized Trial of Lobectomy Versus Limited Resection for T1 N0 Non-Small Cell Lung Cancer." Lung Cancer Study Group Ann Thorac Surg. 1995 September; 60 (3): 615-22. <http://ats.ctsnetjournals.org/cgi/content/full/60/3/615>.

[viii] Landreneau, Sugarbaker, et al. "Wedge Resection Versus Lobectomy for Stage I (T1 N0 M0) Non-Small-Cell Lung Cancer." J Thorac Cardiovasc Surg. 1997 April; 113(4): 691-8; discussion 698-700.

[ix] Warren, W. H. and L. P. Faber. "Segmentectomy Versus Lobectomy in Patients With Stage I Pulmonary Carcinoma." Five-Year Survival and Patterns of Intrathoracic Recurrence. J Thorac Cardiovasc Surg. 1994 April; 107 (4):1087-93.

[x] Landreneau, Sugarbaker, et al. "Wedge Resection Versus Lobectomy for Stage I (T1 N0 M0) Non-Small-Cell Lung Cancer." J Thorac Cardiovasc Surg. 1997 April; 113(4): 691-8; discussion 698-700.

[xi] Kodama, Doi, et al. "Intentional Limited Resection for Selected Patients With T1 N0 M0 Non-Small-Cell Lung Cancer: A Single-Institution Study." J Thorac Cardiovasc Surg. 1997 September; 114 (3):347-53.

[xii] Miller, J. I. and C. R. Hatcher, Jr. "Limited Resection of Bronchogenic Carcinoma in the Patient With Marked Impairment of Pulmonary Function." Ann Thorac Surg. 1987 October; 44(4):340-3.

[xiii] Hilaris, B. S. and D. Nori. "The Role of External Radiation and Brachytherapy in Unresectable Non-Small Cell Lung Cancer." Surg Clin North Am. 1987 October; 67(5):1061-71.

[xiv] Fleischman, Kagan, et al. "Iodine125 Interstitial Brachytherapy in the Treatment of Carcinoma of the Lung." J Surg Oncol. 1992 January; 49(1):25-8.

[xv] National Cancer Institute. "Phase III Randomized Study of Sublobar Resection With Versus Without Intraoperative Brachytherapy in High-Risk Patients With Stage I Non-Small Cell Lung Cancer." Protocol ID NCT00107172, ACOSOG-Z4032 SRCI. <http://www.cancer.gov/clinicaltrials/ACOSOG-Z4032>.

[xvi] Lee, Daly, et al. "Limited Resection for Non-Small Cell Lung Cancer: Observed Local Control With Implantation of $^{125}$I Brachytherapy Seeds." Ann Thorac Surg. 2003 January; 75(1):237-42.

[xvii] Pisch, Panigrahi, et al. "1-125 Volume Implant in Stage I Lung Cancer Patients Medically Unresectable." Endocuriether/Hyperthem Oncology 1996; 12:165-170.

[xviii] Chen, Galloway, et al. "Intraoperative $^{125}$I Brachytherapy for High-Risk Stage I Non-Small Cell Lung Carcinoma." Int J Radiat Oncol Biol Phys. 1999 Jul. 15; 44(5):1057-63.

[xix] Pisch, Belsley, et al. "Placement of $^{125}$I Implants With the Da Vinci Robotic System After Video-Assisted Thoracoscopic Wedge Resection: A Feasibility Study." Int J Radiat Oncol Biol Phys. 2004 Nov. 1; 60(3):928-32.

The invention claimed is:

1. A staple used for brachytherapy delivery in the treatment of cancer by radiation therapy, said staple comprised of:
   a base;
   a radioactive source;
   said base formed as a tubular cavity for receiving and holding said radioactive source therein;
   and tissue piercing ends formed as legs of the staple;
   said staple constructed and arranged so that the legs thereof pierce tissue at a tissue site so as to secure the radioactive source at a fixed position at the tissue site.

2. The staple of claim 1 wherein said staple is constructed and arranged so that the legs thereof pierce tissue in performing a surgical procedure at a surgical margin and further including an array of staples constructed and arranged to extend spaced longitudinally of the surgical margin.

3. The staple of claim 2 wherein said array of staples are for a brachytherapy delivery system that includes a staple applicator for applying a plurality of radioactive sources to the tissue site at the surgical margin.

4. The staple of claim 1 wherein the legs form pointed legs of wire having a diameter between 0.21 mm and 0.5 mm, leg widths ranging from 3 mm to 4 mm, and leg lengths ranging from 2.5 mm to 4.8 mm.

5. The staple of claim 1 wherein said base comprises a sleeve that forms the tubular cavity and said radioactive source includes a radioactive seed, said sleeve accommodating said radioactive seed in said tubular cavity.

6. The staple of claim 5 wherein the radioactive seed is an iodine seed.

7. The staple of claim 1 wherein said base includes a tubular sleeve having an outer diameter on the order of 0.9 mm and an inner diameter on the order of 0.8 mm.

8. The staple of claim 1 wherein the radioactive source is an iodine seed having a length on the order of 4.5 mm.

9. The staple of claim 1 wherein the tubular cavity is defined by a sleeve that is constructed of any one of platinum, titanium, nickel-titanium alloys, gold, stainless steel, palladium, silica and alumina.

10. The staple of claim 1 wherein the legs are fabricated from wires ranging from 0.21 to 0.28 mm diameter, with widths ranging from 3 to 4 mm and leg-lengths ranging from 2.5 to 4.8 mm.

11. The staple of claim 1 wherein said tubular cavity is formed by an encapsulating outer element, and said radioactive source includes a radioactive center element, said outer element encapsulating said radioactive center element.

12. The staple of claim 1 wherein the tubular cavity is formed by a metal tube.

13. The staple of claim 12 wherein the metal tube is one of platinum, titanium, nickel-titanium alloys, gold, stainless steel, palladium, silica and alumina.

14. The staple of claim 12 wherein the metal tube is on the order of 0.40 mm in diameter, with a wall thickness on the order of 0.07 mm, resulting in a cavity of on the order of 0.26 mm diameter.

15. The staple of claim 12 wherein the legs are formed by metal wires engaged with the metal tube.

16. The staple of claim 15 wherein the wires are titanium wires having a diameter on the order of 0.25 mm and laser welded to the metal tube.

17. The staple of claim 1 wherein the radioactive source is for cancer treatment and is characterized by a dose distribution delivery of 125-140 Gy within 1 cm of the staple construction.

18. A combination staple used for brachytherapy delivery in the treatment of cancer by radiation therapy and an applicator for applying the staple, said staple including a base and a radioactive source, said base formed as a sleeve having an elongated cavity for receiving and holding said radioactive source therein, and tissue piercing ends connected with said base and formed as legs of the staple, said staple constructed and arranged so that the legs thereof pierce at a tissue site so as to secure the radioactive source at a fixed position at the tissue site, said applicator constructed and arranged for the support of one or more staples and for applying the staple at the tissue site.

19. The combination of claim 18 including a plurality of staples arranged in a staple array, and said applicator includes an activator for applying each staple.

20. The combination of claim 19 wherein said array of staples is constructed and arranged to extend spaced longitudinally of a surgical margin.

21. The combination of claim 19 wherein said radioactive source includes a radioactive seed, said sleeve accommodating said radioactive seed in said tubular cavity.

22. The staple construction of claim 1 wherein the tubular cavity is formed by a metal tube, and wherein the metal tube is one of platinum, titanium, nickel-titanium alloys, gold, stainless steel, palladium, silica and alumina.

23. A method of forming a staple that is to be used for brachytherapy delivery in the treatment of cancer by radiation therapy, including providing a base and a radioactive source, forming the base as a tubular cavity for receiving and holding the radioactive source therein, providing end wires that serve as tissue piercing legs of the staple, and securing the respective end wires to opposed ends of the tubular base.

24. The method of claim 23 wherein the end wires are secured by laser welding.

25. The staple of claim 1 wherein said tubular cavity is formed by an encapsulating outer element, and said radioactive source includes a radioactive center element, said outer element encapsulating said radioactive center element, and wherein the encapsulating outer element extends from said base and into said legs.

* * * * *